(12) United States Patent
Aoki et al.

(10) Patent No.: US 7,118,898 B1
(45) Date of Patent: Oct. 10, 2006

(54) *RHODOCOCCUS* BACTERIUM, NITRILASE GENE, NITRYLHYDRATASE GENE AND AMIDASE GENE FROM *RHONDOCOCCUS* BACTERIUM, AND PROCESS FOR PRODUCING CARBOXYLIC ACIDS BY USING THEM

(75) Inventors: Hirobumi Aoki, Chiba (JP); Harumi Kamachi, Chiba (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/869,142

(22) PCT Filed: Oct. 25, 2000

(86) PCT No.: PCT/JP00/07464

§ 371 (c)(1),
(2), (4) Date: Jun. 26, 2001

(87) PCT Pub. No.: WO01/30994

PCT Pub. Date: May 3, 2001

(30) Foreign Application Priority Data

| Oct. 26, 1999 | (JP) | ................................. 11-303212 |
| Jan. 26, 2000 | (JP) | ........................... 2000-021797 |
| Apr. 10, 2000 | (JP) | ........................... 2000-107855 |

(51) Int. Cl.
*C12P 7/40* (2006.01)
*C12N 9/02* (2006.01)
*C12N 1/20* (2006.01)
*C12N 15/00* (2006.01)
*C07H 21/04* (2006.01)

(52) U.S. Cl. ...................... 435/136; 435/183; 435/189; 435/252.1; 435/252.3; 435/320.1; 536/23.1; 536/23.2

(58) Field of Classification Search ................. 435/183, 435/189, 252.1, 252.3, 252.33, 320.1; 536/23.1, 536/23.2
See application file for complete search history.

(56) References Cited

U.S. PATENT DOCUMENTS

| 4,629,700 A | * | 12/1986 | Prevatt et al. ............... 435/128 |
| 5,811,286 A | | 9/1998 | Fallon et al. |
| 5,827,699 A | | 10/1998 | Yanenko et al. |

FOREIGN PATENT DOCUMENTS

| EP | 0 445 646 A2 | 9/1991 |
| EP | A2 0 445 646 | 9/1991 |
| EP | 0 502 476 A2 | 9/1992 |
| JP | 2001-136977 A | 5/1991 |
| JP | 7-99980 | 4/1995 |
| JP | 2001069978 | * 3/2001 |
| JP | 2001-292772 A | 10/2001 |
| WO | WO 97/06248 A1 | 2/1997 |
| WO | 0 909 821 A2 | 4/1999 |
| WO | WO01/64857 A1 | 9/2001 |

OTHER PUBLICATIONS

Kato et al. A new enzymic method of nitrile synthesis by *Rhodococcus* sp. strain YH3-3. Journal of Molecular Catalysis B: Enzymatic. vol. 6, Issue 3, Mar. 11, 1999, pp. 249-256.*
Alberts et al. Molecular Biology of the Cell. 3rd ed. New York: Garland Publishing, Inc.; 1994. pp. 325-326*
Bunch. Antonie Van Leeuwenhoek. 1998 Jul.-Oct.;74(1-3):89-97.*
Stevenson et al. Biotechnol Appl Biochem. Jun. 1992;15(3):283-302. (ABSTRACT).*
"Nitrilase from *Rhodococcus Rhodochrous* J1 Sequencing and Overexpression of the Gene and Identification of an Essential Cysteine Residue", Kobayashi et al., The Journal of Biological Chemistry, vol. 267, No. 29, pp. 20746-20751 (1992).
"Amidase couples with low-molecular-mass nitrile hydratase from *Rhodococcus rhodochrous* J1 Sequencing and expression of the gene and purification and characterization of the gene product" Kobayashi et al., Eur. J. Biochem. (1993) vol. 217, No. 1, pp. 327-336.
"Application of whole cell *rhodococcal* biocatalysts in acrylic polymer manufacture" Hughes et al., Antonie van Leeuwenhoek (1998) vol. 74 No. 1-3, pp. 107-118.
Kobayashi, et al., "The Catalytic Mechanism of Amidase Also Involves Nitrile Hydrolysis", *FEBS Letters* (1998), vol. 439, pp. 325-328.
Veiko, et al., "Cloning and Determination of the Nucelotide Sequence of the Nitrile Hydratase Gene", *Russian Biotechnology* (1995), No. 5, pp. 1-4.

(Continued)

Primary Examiner—Tekchand Saidha
Assistant Examiner—Christian L. Fronda
(74) Attorney, Agent, or Firm—Sughrue Mion, PLLC

(57) ABSTRACT

The present invention relates to a novel *Rhodococcus* bacterium and to a process of hydrolyzing a cyano group of a nitrile compound using a novel *Rhodococcus* bacterium to produce the corresponding carboxylic acid. The present invention also relates to a process of producing carboxylic acids, in particular cyano carboxylic acids using a transformant transformed with a plasmid containing a nitrilase gene, a nitrile hydratase gene and an amidase gene derived from *Rhodococcus* bacteria capable of exhibiting particularly excellent position selectivity for the cyano group of aromatic polynitrile compounds, to such a transformant, such a plasmid, to such genes, to a process of producing an enzyme using the transformant, and to enzymes obtained by the process. The carboxylic acids, in particular cyano carboxylic acids obtained by the present invention are useful as starting materials for the synthesis of drugs, agrochemicals, dyestuff and other chemicals.

23 Claims, 6 Drawing Sheets

OTHER PUBLICATIONS

Database Accession No. X86737, retrieved from EBI online.

Kobayashi, et al., "Cloning, Nucleotide Sequence and Expression in *Escherichia coli* of Two Cobalt-containing Nitrile Hydratse Genes from *Rhodococcus rhodochrous* J1", *Biochimica et Biophysica Acta* (1991), vol. 1129, No. 1, pp. 23-33.

Database Accession No. P21219, retrieved from EBI online.

Database Accession No. P21220, retrieved from EBI online.

Nagasawa, et al., "Characterization of a New Cobalt-containing Nitrile Hydratase Purified from Urea-induced Cells of *Rhodococcus rhodochrous* J1", *Eur. J. Biochem* (1991), vol. 196, No. 3, pp. 581-589.

Komeda, et al., "Characterization of the Gene Cluster of High-Molecular-Mass Nitrile Hydratase (H-NHase) Induced by its Reaction Product in *Rhodococcus rhodochrous* J1", *Proc. Natl. Acad. Sci.* (1996), vol. 93, No. 9, pp. 4267-4272.

Database Accession No. D67027, retrieved from EBI online.

Stevenson, et al., "Mechanistic and Structural Studies on *Rhodococcus* ATCC 39484 Nitrilase", *Biotechnology and Applied Biochemistry* (1992), vol. 15, No. 3, pp. 283-302.

Kato, et al., "Nitrile Hydratase Involved in Aldoxime Metabolism from *Rhodococcus* sp. Strain YH3-3: Puirification and Classification", *Eur. J. Biochem.* (1999), vol. 263, pp. 662-670.

Silman, et al., "Directed Evolution of Amidase in *Methylophilus methylotrophus*; Purification and Properties of Amidases from Wild-type and Mutant Strains", *Journal of General Microbiology* (1991), vol. 137, pp. 169-178.

Kobayashi, et al., "Nitrilase Catalyzes Amide Hydrolysis as Well as Nitride Hydrolysis", *Biochemical and Biophysical Research Communications* (1998), vol. 253, pp. 662-666.

A.W. Bunch, "Biotransformatino of Nitriles by *Rhodocicci*", *Antonie van Leewenhoek* (1998),. vol. 74, pp. 89-97.

\* cited by examiner

SEQUENCE LISTING

<160> NUMBER OF SEQ ID NOS: 7

<210> SEQ ID NO 1
<211> LENGTH: 1531
<212> TYPE: DNA
<213> ORGANISM: Rhodococcus sp.
<220> FEATURE:
<221> NAME/KEY: exon
<222> LOCATION: (324)..(1421)
<223> OTHER INFORMATION:

<400> SEQUENCE: 1

```
agcttgacca tgattacgaa ttcgagctcg gtacccgggg atcgaaccag caacggggac      60
gcacagtcga cgtagacctc gacctatccg ccgttccgca gaaggacacc gaccaccacc     120
acttcaacat ccttcaacgt gcccggccag tccttcgacg aatcgaaacg gcgaagagcc     180
gcctcggacc ccccggccga accgctcgat gaactcccct acacgggtgg cgcagaatgc     240
caggacccgt gtcattccac gtcaattcac gcgccttttc acctcgtact gtcctgccaa     300
acacaagcaa cggaggtacg gac atg gtc gaa tac aca aac aca ttc aaa gtt   353
                          Met Val Glu Tyr Thr Asn Thr Phe Lys Val
                            1               5                  10 gct gcg gtg cag gca cag cct gtg tgg ttc gac gcg gcc aaa acg gtc       401
Ala Ala Val Gln Ala Gln Pro Val Trp Phe Asp Ala Ala Lys Thr Val
             15                  20                  25 gac aag acc gtg tcc atc atc gcg gaa gca gcc cgg aac ggg tgc gag       449
Asp Lys Thr Val Ser Ile Ile Ala Glu Ala Ala Arg Asn Gly Cys Glu
         30                  35                  40 ctc gtt gcg ttt ccc gag gta ttc atc ccg ggg tac ccg tac cac atc       497
Leu Val Ala Phe Pro Glu Val Phe Ile Pro Gly Tyr Pro Tyr His Ile
     45                  50                  55 tgg gtc gac agc ccg ctc gcc gga atg gcg aag ttc gcc gtg cgc tac       545
Trp Val Asp Ser Pro Leu Ala Gly Met Ala Lys Phe Ala Val Arg Tyr
 60                  65                  70
```

```
cac gag aat tcc ctg acg atg gac agc ccg cac gta cag cgg ttg ctc      593
His Glu Asn Ser Leu Thr Met Asp Ser Pro His Val Gln Arg Leu Leu
 75                  80                  85                  90 gat gcc gcc cgc gac cac aac atc gcc gta gtg gtg gga atc agc gag      641
Asp Ala Ala Arg Asp His Asn Ile Ala Val Val Val Gly Ile Ser Glu
                 95                 100                 105 cgg gat ggc ggc agc ttg tac atg acc cag ctc atc atc gac gcc gat      689
Arg Asp Gly Gly Ser Leu Tyr Met Thr Gln Leu Ile Ile Asp Ala Asp
             110                 115                 120 ggg caa ctg gtc gcc cga cgc cgc aag ctc aag ccc acc cac gtc gag      737
Gly Gln Leu Val Ala Arg Arg Arg Lys Leu Lys Pro Thr His Val Glu
         125                 130                 135 cgt tcg gta tac gga gaa gga aac ggc tcg gat atc tcc gtg tac gac      785
Arg Ser Val Tyr Gly Glu Gly Asn Gly Ser Asp Ile Ser Val Tyr Asp
    140                 145                 150 atg cct ttc gca cgg ctt ggc gcg ctc aac tgc tgg gag cat ttc cag      833
Met Pro Phe Ala Arg Leu Gly Ala Leu Asn Cys Trp Glu His Phe Gln
155                 160                 165                 170 acg ctc acc aag tac gca atg tac tcg atg cac gag cag gtg cac gtc      881
Thr Leu Thr Lys Tyr Ala Met Tyr Ser Met His Glu Gln Val His Val
                175                 180                 185 gcg agc tgg cct ggc atg tcg ctg tac cag ccg gag gtc ccc gca ttc      929
Ala Ser Trp Pro Gly Met Ser Leu Tyr Gln Pro Glu Val Pro Ala Phe
            190                 195                 200 ggt gtc gat gcc cag ctc acg gcc acg cgt atg tac gca ctc gag gga      977
Gly Val Asp Ala Gln Leu Thr Ala Thr Arg Met Tyr Ala Leu Glu Gly
        205                 210                 215 caa acc ttc gtg gtc tgc acc acc cag gtg gtc aca ccg gag gcc cac     1025
Gln Thr Phe Val Val Cys Thr Thr Gln Val Val Thr Pro Glu Ala His
220                 225                 230 gag ttc ttc tgc gag aac gag gaa cag cga atg ttg atc ggc cga ggc     1073
Glu Phe Phe Cys Glu Asn Glu Glu Gln Arg Met Leu Ile Gly Arg Gly
235                 240                 245                 250 gga ggt ttc gcg cgc atc atc ggg ccc gac ggc cgc gat ctc gca act     1121
Gly Gly Phe Ala Arg Ile Ile Gly Pro Asp Gly Arg Asp Leu Ala Thr
                255                 260                 265 cct ctc gcc gaa gat gag gag ggg atc ctc tac gcc gac atc gat ctg     1169
Pro Leu Ala Glu Asp Glu Glu Gly Ile Leu Tyr Ala Asp Ile Asp Leu
            270                 275                 280 tct gcg atc acc ttg gcg aag cag gcc gct gac ccc gtg ggc cac tac     1217
Ser Ala Ile Thr Leu Ala Lys Gln Ala Ala Asp Pro Val Gly His Tyr
        285                 290                 295 tca cgg ccg gat gtg ctg tcg ctg aac ttc aac cag cgc cgc acc acg     1265
Ser Arg Pro Asp Val Leu Ser Leu Asn Phe Asn Gln Arg Arg Thr Thr
300                 305                 310 ccc gtc aac acc cca ctt tcc acc atc cat gcc acg cac acg ttc gtg     1313
Pro Val Asn Thr Pro Leu Ser Thr Ile His Ala Thr His Thr Phe Val
315                 320                 325                 330 ccg cag ttc ggg gca ctc gac ggc gtc cgt gag ctc aac gga gcg gac     1361
Pro Gln Phe Gly Ala Leu Asp Gly Val Arg Glu Leu Asn Gly Ala Asp
                335                 340                 345 gaa cag cgc gca ttg ccc tcc aca cat tcc gac gag acg gac cgg gcg     1409
Glu Gln Arg Ala Leu Pro Ser Thr His Ser Asp Glu Thr Asp Arg Ala
            350                 355                 360 aca gcc acc ctc tgactcgggc gcacccgtgg cgcctccgaa gcgccacggg         1461
Thr Ala Thr Leu
            365 tgtgtgaagg ggcgagacag gggaatcgga ggatccccgg gtaccgagct cgaattcgta   1521
```

-continued atcatggtca　　1531

<210> SEQ ID NO 2
<211> LENGTH: 366
<212> TYPE: PRT
<213> ORGANISM: Rhodococcus sp.

<400> SEQUENCE: 2

```
Met Val Glu Tyr Thr Asn Thr Phe Lys Val Ala Ala Val Gln Ala Gln
1               5                   10                  15

Pro Val Trp Phe Asp Ala Ala Lys Thr Val Asp Lys Thr Val Ser Ile
            20                  25                  30

Ile Ala Glu Ala Ala Arg Asn Gly Cys Glu Leu Val Ala Phe Pro Glu
        35                  40                  45

Val Phe Ile Pro Gly Tyr Pro Tyr His Ile Trp Val Asp Ser Pro Leu
    50                  55                  60

Ala Gly Met Ala Lys Phe Ala Val Arg Tyr His Glu Asn Ser Leu Thr
65                  70                  75                  80

Met Asp Ser Pro His Val Gln Arg Leu Leu Asp Ala Ala Arg Asp His
                85                  90                  95

Asn Ile Ala Val Val Gly Ile Ser Glu Arg Asp Gly Gly Ser Leu
            100                 105                 110

Tyr Met Thr Gln Leu Ile Ile Asp Ala Asp Gly Gln Leu Val Ala Arg
        115                 120                 125

Arg Arg Lys Leu Lys Pro Thr His Val Glu Arg Ser Val Tyr Gly Glu
    130                 135                 140

Gly Asn Gly Ser Asp Ile Ser Val Tyr Asp Met Pro Phe Ala Arg Leu
145                 150                 155                 160

Gly Ala Leu Asn Cys Trp Glu His Phe Gln Thr Leu Thr Lys Tyr Ala
                165                 170                 175

Met Tyr Ser Met His Glu Gln Val His Val Ala Ser Trp Pro Gly Met
            180                 185                 190

Ser Leu Tyr Gln Pro Glu Val Pro Ala Phe Gly Val Asp Ala Gln Leu
        195                 200                 205

Thr Ala Thr Arg Met Tyr Ala Leu Glu Gly Gln Thr Phe Val Val Cys
    210                 215                 220

Thr Thr Gln Val Val Thr Pro Glu Ala His Glu Phe Phe Cys Glu Asn
225                 230                 235                 240

Glu Glu Gln Arg Met Leu Ile Gly Arg Gly Gly Phe Ala Arg Ile
                245                 250                 255

Ile Gly Pro Asp Gly Arg Asp Leu Ala Thr Pro Leu Ala Glu Asp Glu
            260                 265                 270

Glu Gly Ile Leu Tyr Ala Asp Ile Asp Leu Ser Ala Ile Thr Leu Ala
        275                 280                 285

Lys Gln Ala Ala Asp Pro Val Gly His Tyr Ser Arg Pro Asp Val Leu
    290                 295                 300

Ser Leu Asn Phe Asn Gln Arg Arg Thr Thr Pro Val Asn Thr Pro Leu
305                 310                 315                 320

Ser Thr Ile His Ala Thr His Thr Phe Val Pro Gln Phe Gly Ala Leu
                325                 330                 335

Asp Gly Val Arg Glu Leu Asn Gly Ala Asp Glu Gln Arg Ala Leu Pro
            340                 345                 350

Ser Thr His Ser Asp Glu Thr Asp Arg Ala Thr Ala Thr Leu
        355                 360                 365
```

<210> SEQ ID NO 3
<211> LENGTH: 2822
<212> TYPE: DNA
<213> ORGANISM: Rhodococcus sp.
<220> FEATURE:
<221> NAME/KEY: CDS
<222> LOCATION: (1379)..(2068)
<223> OTHER INFORMATION: nitrile hydratase beta subunit
<221> NAME/KEY: CDS
<222> LOCATION: (2082)..(2693)
<223> OTHER INFORMATION: nitrile hydratase alpha subunit

<400> SEQUENCE: 3

| | |
|---|---:|
| ctagaggatc tcggtcatcg cgataccatc gttgcggacg atgatgtcca atacgtacca | 60 |
| ctggtccgcg gtcaacttct cttgatcgac cacgttatgg attctacgac tcagggaccg | 120 |
| gctcacggct tccagggcgc ctccgaccaa aggtgatcga acgacatttc cggattcagc | 180 |
| caccgcttcc gactcgatca ttcctgtccc tccccgtcca cgcgcagttg atcttacctc | 240 |
| ctcatcaaga ggatatccac tgaacgaatt atttcaagtg gaagtacttg gagtcgatcc | 300 |
| tacacgtgag tggacgatgc ctgggcgcta gtcggatgtg caaccaccc acccctcct | 360 |
| cccgcctacg ccgaagaccg gaaccggcgt cgtccctgcc tgccgtctct ggcaactgtt | 420 |
| gtgaacgccc gagcggccct cacggctctt cagttggcgc ggatcgccat gcggacgtc | 480 |
| gcccacggcg ggacctacgc atcttcggcc ggaaggcagc cgccggtcacg aacacctagc | 540 |
| ggcagtcgag cacctgagac gaaggccgcc ggcgtcctgt cccggaaatc cgcagcccag | 600 |
| ccgtgacagc caacagtcgt ggcggttccc tcccctccta gggtctttga ctcggcgcca | 660 |
| acgcctgcga gggcgctcgt cgcggaccac ttgtcgaggt cggtgccgca cgtcaccgag | 720 |
| cgcacccttc ttcgtgctct gcgcatcggc ccggaccgcg accgcggcaa cactacgacg | 780 |
| tctgacaatg ctgatccct gccgccgccg ttggacgacc acagttgcta cgagcatgcg | 840 |
| gagccaacca taggcatcat gcgatcgccg gagtcttcat cctattttgg gatgcgcagg | 900 |
| attaacacat ctacacattg acatccgttc gatgtgaag taaaaattgt cacgtagggc | 960 |
| ggcaggcgaa gtctgcagct cgaacatcga agggtgggag ccgagagatc ggagacgcag | 1020 |
| acacccggag ggaacttagc ctcccggacc gatgcgtgtc ctggcaacgc tcaagattc | 1080 |
| agcgcaagcg attcaatctt gttacttcca gaaccgaatc acgtccccgt agtgtgcggg | 1140 |
| gagagcgccc gaacgcaggg atggtatcca tgcgccccct ctcttttcga acgagaaccg | 1200 |
| gccggtacag tcaatccgga cacattgtga cgccgttcaa cgattgttgt gctgtgaagg | 1260 |
| attcactcaa gccaactgat atcgccattc cgttgccgga acatttgacg ccttctccct | 1320 |
| acgagtagaa gccagctgga ccctctttga gcccagctcc gatgaaagga atgaggaa | 1378 |
| atg gat ggt atc cac gac aca ggc ggc atg acc gga tac gga ccg gtc<br>Met Asp Gly Ile His Asp Thr Gly Gly Met Thr Gly Tyr Gly Pro Val<br>1               5                 10               15 | 1426 |
| ccc tat cag aag gac gag ccc ttc ttc cac tac gag tgg gag ggt cga<br>Pro Tyr Gln Lys Asp Glu Pro Phe Phe His Tyr Glu Trp Glu Gly Arg<br>               20                 25                 30 | 1474 |
| acc ctg tcg att ctg acc tgg atg cat ctc aag ggc atg tcg tgg tgg<br>Thr Leu Ser Ile Leu Thr Trp Met His Leu Lys Gly Met Ser Trp Trp<br>          35                 40                 45 | 1522 |
| gac aag tcg cgg ttc ttc cgg gag tcg atg ggg aac gaa aac tac gtc<br>Asp Lys Ser Arg Phe Phe Arg Glu Ser Met Gly Asn Glu Asn Tyr Val<br>50                55                 60 | 1570 |
| aac gag att cgc aac tcg tac tac acc cac tgg ctg agt gcg gcg gaa<br>Asn Glu Ile Arg Asn Ser Tyr Tyr Thr His Trp Leu Ser Ala Ala Glu | 1618 |

| | | | | | | | | | | | | | | | | |
|---|---|---|---|---|---|---|---|---|---|---|---|---|---|---|---|---|
| | | 65 | | | | | 70 | | | | | 75 | | | | 80 |
| cgt | atc | ctc | gtc | gcc | gac | aag | atc | atc | acc | gaa | gaa | gag | cga | aag | cac | 1666 |
| Arg | Ile | Leu | Val | Ala | Asp | Lys | Ile | Ile | Thr | Glu | Glu | Glu | Arg | Lys | His | |
| | | | | 85 | | | | | 90 | | | | | 95 | | |
| cgc | gtg | cag | gag | atc | ctc | gag | ggt | cgg | tac | acg | gac | agg | aac | ccg | tcg | 1714 |
| Arg | Val | Gln | Glu | Ile | Leu | Glu | Gly | Arg | Tyr | Thr | Asp | Arg | Asn | Pro | Ser | |
| | | | 100 | | | | | 105 | | | | | 110 | | | |
| cgg | aag | ttc | gat | ccg | gcc | gag | atc | gag | aag | gcg | atc | gag | agg | ctt | cac | 1762 |
| Arg | Lys | Phe | Asp | Pro | Ala | Glu | Ile | Glu | Lys | Ala | Ile | Glu | Arg | Leu | His | |
| | | 115 | | | | | 120 | | | | | 125 | | | | |
| gag | ccc | cac | tcc | cta | gtg | ctt | cca | gga | gcg | gag | ccg | agt | ttc | tcc | ctc | 1810 |
| Glu | Pro | His | Ser | Leu | Val | Leu | Pro | Gly | Ala | Glu | Pro | Ser | Phe | Ser | Leu | |
| 130 | | | | | 135 | | | | | 140 | | | | | | |
| ggt | gac | aag | gtc | aaa | gtg | aag | aac | atg | aac | ccg | ctg | gga | cac | aca | cgg | 1858 |
| Gly | Asp | Lys | Val | Lys | Val | Lys | Asn | Met | Asn | Pro | Leu | Gly | His | Thr | Arg | |
| 145 | | | | | 150 | | | | | 155 | | | | | 160 | |
| tgc | ccg | aag | tat | gtg | cgg | aac | aga | atc | ggg | gaa | atc | gtc | acc | tcc | cac | 1906 |
| Cys | Pro | Lys | Tyr | Val | Arg | Asn | Arg | Ile | Gly | Glu | Ile | Val | Thr | Ser | His | |
| | | | | 165 | | | | | 170 | | | | | 175 | | |
| ggg | tgc | cag | atc | tat | ccc | gag | agc | agc | tcc | gcc | ggc | ctc | ggc | gac | gat | 1954 |
| Gly | Cys | Gln | Ile | Tyr | Pro | Glu | Ser | Ser | Ser | Ala | Gly | Leu | Gly | Asp | Asp | |
| | | | 180 | | | | | 185 | | | | | 190 | | | |
| ccc | cgc | ccg | ctc | tac | acg | gtc | gcg | ttt | tcc | gcc | cag | gaa | ctg | tgg | ggc | 2002 |
| Pro | Arg | Pro | Leu | Tyr | Thr | Val | Ala | Phe | Ser | Ala | Gln | Glu | Leu | Trp | Gly | |
| | | 195 | | | | | 200 | | | | | 205 | | | | |
| gac | gac | gga | aac | ggg | aaa | gac | gta | gtg | tgc | gtc | gat | ctc | tgg | gaa | ccg | 2050 |
| Asp | Asp | Gly | Asn | Gly | Lys | Asp | Val | Val | Cys | Val | Asp | Leu | Trp | Glu | Pro | |
| | 210 | | | | | 215 | | | | | 220 | | | | | |
| tac | ctg | atc | tct | gcg | tga | aaggaatacg | | ata | gtg | agc | gag | cac | gtc | aat | | 2099 |
| Tyr | Leu | Ile | Ser | Ala | | | | | Val | Ser | Glu | His | Val | Asn | | |
| 225 | | | | | | | | | | 230 | | | | | 235 | |
| aag | tac | acg | gag | tac | gag | gca | cgt | acc | aag | gca | atc | gaa | acc | ttg | ctg | 2147 |
| Lys | Tyr | Thr | Glu | Tyr | Glu | Ala | Arg | Thr | Lys | Ala | Ile | Glu | Thr | Leu | Leu | |
| | | | | 240 | | | | | 245 | | | | | 250 | | |
| tac | gag | cga | ggg | ctc | atc | acg | ccc | gcc | gcg | gtc | gac | cga | gtc | gtt | tcg | 2195 |
| Tyr | Glu | Arg | Gly | Leu | Ile | Thr | Pro | Ala | Ala | Val | Asp | Arg | Val | Val | Ser | |
| | | | 255 | | | | | 260 | | | | | 265 | | | |
| tac | tac | gag | aac | gag | atc | ggc | ccg | atg | ggc | ggt | gcc | aag | gtc | gtg | gcc | 2243 |
| Tyr | Tyr | Glu | Asn | Glu | Ile | Gly | Pro | Met | Gly | Gly | Ala | Lys | Val | Val | Ala | |
| | | 270 | | | | | 275 | | | | | 280 | | | | |
| aag | tcc | tgg | gtg | gac | cct | gag | tac | cgc | aag | tgg | ctc | gaa | gaa | gac | gcg | 2291 |
| Lys | Ser | Trp | Val | Asp | Pro | Glu | Tyr | Arg | Lys | Trp | Leu | Glu | Glu | Asp | Ala | |
| 285 | | | | | 290 | | | | | 295 | | | | | | |
| acg | gcc | gcg | atg | gcg | tca | ttg | ggc | tat | gcc | ggc | gag | cag | gca | cac | cag | 2339 |
| Thr | Ala | Ala | Met | Ala | Ser | Leu | Gly | Tyr | Ala | Gly | Glu | Gln | Ala | His | Gln | |
| 300 | | | | | 305 | | | | | 310 | | | | | 315 | |
| atc | tcg | gcc | gtc | ttc | aac | gac | tcc | caa | aca | cat | cac | gta | gtg | gtg | tgc | 2387 |
| Ile | Ser | Ala | Val | Phe | Asn | Asp | Ser | Gln | Thr | His | His | Val | Val | Val | Cys | |
| | | | | 320 | | | | | 325 | | | | | 330 | | |
| act | ctg | tgt | tcg | tgc | tat | ccg | tgg | ccg | gtg | ctt | ggc | ctc | ccg | ccc | gcc | 2435 |
| Thr | Leu | Cys | Ser | Cys | Tyr | Pro | Trp | Pro | Val | Leu | Gly | Leu | Pro | Pro | Ala | |
| | | | 335 | | | | | 340 | | | | | 345 | | | |
| tgg | tac | aag | agc | atg | gag | tac | cgg | tcc | cga | gtg | gta | gca | gac | cct | cgt | 2483 |
| Trp | Tyr | Lys | Ser | Met | Glu | Tyr | Arg | Ser | Arg | Val | Val | Ala | Asp | Pro | Arg | |
| | | 350 | | | | | 355 | | | | | 360 | | | | |
| gga | gta | ctc | aag | cgc | gat | ttc | ggg | ttc | gac | atc | ccc | gat | gag | gtg | gag | 2531 |
| Gly | Val | Leu | Lys | Arg | Asp | Phe | Gly | Phe | Asp | Ile | Pro | Asp | Glu | Val | Glu | |
| | 365 | | | | | 370 | | | | | 375 | | | | | |
| gtc | agg | gtt | tgg | gac | agc | agc | tcc | gaa | atc | cgc | tac | atc | gtc | atc | ccg | 2579 |

-continued

```
Val Arg Val Trp Asp Ser Ser Glu Ile Arg Tyr Ile Val Ile Pro
380                 385                 390                 395 gaa cgg ccg gcc ggc acc gac ggt tgg tcc gag gac gag ctg gcg aag      2627
Glu Arg Pro Ala Gly Thr Asp Gly Trp Ser Glu Asp Glu Leu Ala Lys
                    400                 405                 410 ctg gtg agt cgg gac tcg atg atc ggt gtc agt aat gcg ctc aca ccg      2675
Leu Val Ser Arg Asp Ser Met Ile Gly Val Ser Asn Ala Leu Thr Pro
                415                 420                 425 cag gaa gtg atc gta tga gtgaagacac actcactgat cggctcccgg             2723
Gln Glu Val Ile Val
        430 cgactgggac cgccgcaccg ccccgcgaca atggcgagct tgtattcacc gagccttggg    2783 aagcaacggc attcggggtc gccatcgcgc tttcggatc                           2822
```

<210> SEQ ID NO 4
<211> LENGTH: 229
<212> TYPE: PRT
<213> ORGANISM: Rhodococcus sp.

<400> SEQUENCE: 4

```
Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
                20                  25                  30

Thr Leu Ser Ile Leu Thr Trp Met His Leu Lys Gly Met Ser Trp Trp
            35                  40                  45

Asp Lys Ser Arg Phe Phe Arg Glu Ser Met Gly Asn Glu Asn Tyr Val
        50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Asn Pro Ser
            100                 105                 110

Arg Lys Phe Asp Pro Ala Glu Ile Glu Lys Ala Ile Glu Arg Leu His
        115                 120                 125

Glu Pro His Ser Leu Val Leu Pro Gly Ala Glu Pro Ser Phe Ser Leu
    130                 135                 140

Gly Asp Lys Val Lys Val Lys Asn Met Asn Pro Leu Gly His Thr Arg
145                 150                 155                 160

Cys Pro Lys Tyr Val Arg Asn Arg Ile Gly Glu Ile Val Thr Ser His
                165                 170                 175

Gly Cys Gln Ile Tyr Pro Glu Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225
```

<210> SEQ ID NO 5
<211> LENGTH: 203
<212> TYPE: PRT
<213> ORGANISM: Rhodococcus sp.

<400> SEQUENCE: 5

-continued

```
Val Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
                20                  25                  30

Val Asp Arg Val Val Ser Tyr Tyr Glu Asn Glu Ile Gly Pro Met Gly
            35                  40                  45

Gly Ala Lys Val Val Ala Lys Ser Trp Val Asp Pro Glu Tyr Arg Lys
        50                  55                  60

Trp Leu Glu Glu Asp Ala Thr Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Cys Thr Leu Cys Ser Cys Tyr Pro Trp Pro Val
                100                 105                 110

Leu Gly Leu Pro Pro Ala Trp Tyr Lys Ser Met Glu Tyr Arg Ser Arg
            115                 120                 125

Val Val Ala Asp Pro Arg Gly Val Leu Lys Arg Asp Phe Gly Phe Asp
        130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190

Ser Asn Ala Leu Thr Pro Gln Glu Val Ile Val
            195                 200
```

```
<210> SEQ ID NO 6
<211> LENGTH: 2822
<212> TYPE: DNA
<213> ORGANISM: Rhodococcus sp.
<220> FEATURE:
<221> NAME/KEY: misc_feature
<222> LOCATION: (556)..(556)
<223> OTHER INFORMATION: "n" may be a, c, g or t
<221> NAME/KEY: misc_feature
<222> LOCATION: (592)..(592)
<223> OTHER INFORMATION: "n" may be a, c, g or t
<221> NAME/KEY: misc_feature
<222> LOCATION: (896)..(896)
<223> OTHER INFORMATION: "n" may be a, c, g or t
<221> NAME/KEY: CDS
<222> LOCATION: (1094)..(2491)
<223> OTHER INFORMATION: amidase

<400> SEQUENCE: 6
tgattacgaa ttcgagctcg gtacccgggg atcacttcgg ccagagggtg acggcgaaat    60
cgggcctcga tctccgcgtc cacggcgttg atacgtgtgt cgaggtcgat caccgcctgc   120
gccaattcgg cgaccagttc ggcagcgaca tcttccccg gcaaccgcac ggtctgcgcc    180
ttcgcggcgg tgactgcggc ccggcgatc gattcggcgt ggcgcacccc ggccccggtg    240
agcattgcgg ccagtcgggc cgccccgacg cggcggatcg ctttcggtcg ctggtagcgg    300
gccagcagca ccacccagcc ccggtccgag gagatctgcg cgacgcgttc gagtccgggg    360
cagatcgcga cgagttgctg acgcagccgg ttgatggtcc gggtacggtc ggcgaccaga    420
tcggtgcggt ggccggtgag catctgcagc tcacgatca actcgtcgt gggacgcaga     480 acgggcaggt ccgaccgcat ccgggactga tcggcgatca cccgggcgtc gcgggcgtcg   540
```

-continued

```
gtcttggctt cgccgncgcg gtagaccgac gatgcctgcc acaccgaacg tncggacagg      600
tagcgcaccg gtttccggc gtcggccagc acagtcagca acaaggtgac gtaggcggtg       660
gtcagatcca ccgtccacga caccgtctcg gtgagtgcgt cgatctcggt gatcaccgca      720
cggatcgttg cttcgtcgtt gtcacatcgc cgcgacagca ccaccgtccc ggaggtgtcg      780
agtacgcata tccagtggtg ttctttgccg acgtcgactc ctgcccacag ttgcgaaccg      840
gtcatcggat ttcctcgttt tcgcttgtgt tccggcctgg ccccgatgga cgcctncgcc      900
ggcatttcct taaacaagcg atcatgcgca gatctcaatc agcggtccag aggtgtccag      960
acaggtcggg tggccagtcc tttcaagccc actcgagag tgggcaaacc ttatgcagcc      1020
tcgccggcct gcccgggtta cagctcaacg taactctcac gaagtaactg cacctacgaa    1080
```

| | | | | | | | | | | |
|---|---|---|---|---|---|---|---|---|---|---|
| cttaaggaac | ctc | atg | tct | tcg | ttg | act | ccc | ccc | aat | tcc  aac  caa  atg  1129 |
| | | Met | Ser | Ser | Leu | Thr | Pro | Pro | Asn | Ser  Asn  Gln  Met |
| | | 1 | | | 5 | | | | | 10 |

| tcg | gcc | ctg | aac | aac | cac | ttc | cga | ttc | gga | ctg | acg | acg | ccg | gaa | ctc | 1177 |
|---|---|---|---|---|---|---|---|---|---|---|---|---|---|---|---|---|
| Ser | Ala | Leu | Asn | Asn | His | Phe | Arg | Phe | Gly | Leu | Thr | Thr | Pro | Glu | Leu | |
| | 15 | | | | 20 | | | | | 25 | | | | | | |

| gaa | gag | ttc | gca | ccg | gcc | ctc | gaa | gcg | acg | ctc | gcg | tcc | tcc | gaa | acc | 1225 |
|---|---|---|---|---|---|---|---|---|---|---|---|---|---|---|---|---|
| Glu | Glu | Phe | Ala | Pro | Ala | Leu | Glu | Ala | Thr | Leu | Ala | Ser | Ser | Glu | Thr | |
| | 30 | | | | | 35 | | | | | 40 | | | | | |

| gtc | gaa | cgc | ctc | tac | gag | cgc | acc | gcg | ccc | gag | ccg | cct | cag | cgg | tca | 1273 |
|---|---|---|---|---|---|---|---|---|---|---|---|---|---|---|---|---|
| Val | Glu | Arg | Leu | Tyr | Glu | Arg | Thr | Ala | Pro | Glu | Pro | Pro | Gln | Arg | Ser | |
| 45 | | | | | 50 | | | | | 55 | | | | | 60 | |

| tgg | acc | tca | ccc | acg | gcg | gac | gag | aac | ccg | ctg | agc | gcc | tgg | tac | gtc | 1321 |
|---|---|---|---|---|---|---|---|---|---|---|---|---|---|---|---|---|
| Trp | Thr | Ser | Pro | Thr | Ala | Asp | Glu | Asn | Pro | Leu | Ser | Ala | Trp | Tyr | Val | |
| | | | 65 | | | | | 70 | | | | | 75 | | | |

| acc | acc | tcg | atc | agc | gaa | acc | gac | gaa | ggc | ccc | ctc | gcc | ggg | cga | acg | 1369 |
|---|---|---|---|---|---|---|---|---|---|---|---|---|---|---|---|---|
| Thr | Thr | Ser | Ile | Ser | Glu | Thr | Asp | Glu | Gly | Pro | Leu | Ala | Gly | Arg | Thr | |
| | | | 80 | | | | | 85 | | | | | 90 | | | |

| gtc | gcc | gtg | aaa | gac | aac | gtc | gca | gtc | gcc | ggc | gtg | ccg | atg | atg | aac | 1417 |
|---|---|---|---|---|---|---|---|---|---|---|---|---|---|---|---|---|
| Val | Ala | Val | Lys | Asp | Asn | Val | Ala | Val | Ala | Gly | Val | Pro | Met | Met | Asn | |
| | | 95 | | | | | 100 | | | | | 105 | | | | |

| ggc | tcc | cga | acc | gtc | gag | ggc | ttc | acc | ccc | cgc | tac | gac | gcc | acc | gtc | 1465 |
|---|---|---|---|---|---|---|---|---|---|---|---|---|---|---|---|---|
| Gly | Ser | Arg | Thr | Val | Glu | Gly | Phe | Thr | Pro | Arg | Tyr | Asp | Ala | Thr | Val | |
| | 110 | | | | | 115 | | | | | 120 | | | | | |

| gta | cgc | cga | ctg | ctc | gac | gcc | ggc | gca | acc | atc | acc | ggc | aaa | gcg | gtg | 1513 |
|---|---|---|---|---|---|---|---|---|---|---|---|---|---|---|---|---|
| Val | Arg | Arg | Leu | Leu | Asp | Ala | Gly | Ala | Thr | Ile | Thr | Gly | Lys | Ala | Val | |
| 125 | | | | 130 | | | | | 135 | | | | | 140 | | |

| tgc | gaa | gat | ctc | tgc | ttc | tcc | ggc | gcc | agc | ttc | act | tcc | cac | ccc | cag | 1561 |
|---|---|---|---|---|---|---|---|---|---|---|---|---|---|---|---|---|
| Cys | Glu | Asp | Leu | Cys | Phe | Ser | Gly | Ala | Ser | Phe | Thr | Ser | His | Pro | Gln | |
| | | | 145 | | | | | 150 | | | | | 155 | | | |

| ccg | gtc | cgc | aac | ccc | tgg | gac | gaa | agc | cgc | atc | acc | ggc | ggc | tcg | tcc | 1609 |
|---|---|---|---|---|---|---|---|---|---|---|---|---|---|---|---|---|
| Pro | Val | Arg | Asn | Pro | Trp | Asp | Glu | Ser | Arg | Ile | Thr | Gly | Gly | Ser | Ser | |
| | | 160 | | | | | 165 | | | | | 170 | | | | |

| agc | ggc | agc | ggc | gcc | ctg | gtc | gcc | agc | ggc | cag | gtg | gat | atg | gca | gtc | 1657 |
|---|---|---|---|---|---|---|---|---|---|---|---|---|---|---|---|---|
| Ser | Gly | Ser | Gly | Ala | Leu | Val | Ala | Ser | Gly | Gln | Val | Asp | Met | Ala | Val | |
| | 175 | | | | | 180 | | | | | 185 | | | | | |

| ggc | ggc | gac | cag | ggc | ggt | tcg | atc | cgc | atc | ccc | gcc | gcg | ttc | tgc | ggc | 1705 |
|---|---|---|---|---|---|---|---|---|---|---|---|---|---|---|---|---|
| Gly | Gly | Asp | Gln | Gly | Gly | Ser | Ile | Arg | Ile | Pro | Ala | Ala | Phe | Cys | Gly | |
| | 190 | | | | | 195 | | | | | 200 | | | | | |

| atc | gtc | gga | cac | aaa | ccc | acc | cac | gga | ctg | gtc | ccc | tat | acg | gga | gca | 1753 |
|---|---|---|---|---|---|---|---|---|---|---|---|---|---|---|---|---|
| Ile | Val | Gly | His | Lys | Pro | Thr | His | Gly | Leu | Val | Pro | Tyr | Thr | Gly | Ala | |
| 205 | | | | 210 | | | | | 215 | | | | | 220 | | |

| ttt | ccc | atc | gaa | cga | acc | atc | gac | cac | ctc | ggt | ccg | atg | acg | cgc | acg | 1801 |
|---|---|---|---|---|---|---|---|---|---|---|---|---|---|---|---|---|
| Phe | Pro | Ile | Glu | Arg | Thr | Ile | Asp | His | Leu | Gly | Pro | Met | Thr | Arg | Thr | |
| | | | 225 | | | | | 230 | | | | | 235 | | | |

| gtc | agc | gac | gcc | gcc | gca | atg | ctc | acc | gtc | ctc | gcc | ggc | acc | gac | ggc | 1849 |
|---|---|---|---|---|---|---|---|---|---|---|---|---|---|---|---|---|

```
Val Ser Asp Ala Ala Met Leu Thr Val Leu Ala Gly Thr Asp Gly
            240                 245                 250 ctc gat ccc cga cag acc cac cgg atc gaa ccg gtg gac tac ctc gcg      1897
Leu Asp Pro Arg Gln Thr His Arg Ile Glu Pro Val Asp Tyr Leu Ala
        255                 260                 265 gcg ctg gcc gaa ccc gca tcg ggt ctg cgc gtg ggt gtg gtc acc gaa      1945
Ala Leu Ala Glu Pro Ala Ser Gly Leu Arg Val Gly Val Val Thr Glu
    270                 275                 280 ggc ttc gac acc cct gtc tcc gac gct gcc gtc gac aat gcc gtg cgc      1993
Gly Phe Asp Thr Pro Val Ser Asp Ala Ala Val Asp Asn Ala Val Arg
285                 290                 295                 300 acc gcc atc ggc gta ctg cgc tcg gcc gga ctt acc gtc gaa gag gtc      2041
Thr Ala Ile Gly Val Leu Arg Ser Ala Gly Leu Thr Val Glu Glu Val
                305                 310                 315 tcg atc ccc tgg cac ctc gat gcg atg gcc gtc tgg aac gtg atc gac      2089
Ser Ile Pro Trp His Leu Asp Ala Met Ala Val Trp Asn Val Ile Asp
            320                 325                 330 cgg gcc gac gac gaa ttc gaa gcc ttc ctg ctg cag gtg ctc gac gag      2137
Arg Ala Asp Asp Glu Phe Glu Ala Phe Leu Leu Gln Val Leu Asp Glu
        335                 340                 345 aac gcc gtc acc atc ccc gaa ctc gga cag gtg cgg gcg cag acg ccg      2185
Asn Ala Val Thr Ile Pro Glu Leu Gly Gln Val Arg Ala Gln Thr Pro
    350                 355                 360 cgc tcg tgg tgc tca cct cga acc gca ccc gcg agg tgc acg acg ccc      2233
Arg Ser Trp Cys Ser Pro Arg Thr Ala Pro Ala Arg Cys Thr Thr Pro
365                 370                 375                 380 tca aac gcc gct gcc tgt acc act ggc tcg aac acc ccg acc tcg cgc      2281
Ser Asn Ala Ala Ala Cys Thr Thr Gly Ser Asn Thr Pro Thr Ser Arg
                385                 390                 395 ggg aag tgg aga tcc tgc gcc gcc gca tcc cgg gca tcg acg aac acc      2329
Gly Lys Trp Arg Ser Cys Ala Ala Ala Ser Arg Ala Ser Thr Asn Thr
            400                 405                 410 tcg cgg cgc agg tcg ccc acg ccg tgc agg cca tgc gcg gga tgg acc      2377
Ser Arg Arg Arg Ser Pro Thr Pro Cys Arg Pro Cys Ala Gly Trp Thr
        415                 420                 425 tgc tca aac cac ccg ggg tcg cgg agt cgc tgg act ggg cac gag cgc      2425
Cys Ser Asn His Pro Gly Ser Arg Ser Arg Trp Thr Gly His Glu Arg
    430                 435                 440 tgc ggg aac tcg acc gcg acg tgc tcg acg cga cga ccg cgg ccg cga      2473
Cys Gly Asn Ser Thr Ala Thr Cys Ser Thr Arg Arg Pro Arg Pro Arg
445                 450                 455                 460 ccc tcg gtg ccg tcc tga agtaccggga ggacctcgac cgagtggtcc             2521
Pro Ser Val Pro Ser
                465 gcaccgggct cgaccggctc ctgacggggt gacagcggcg atgacgacga ccaccgacgc    2581 cggggggttcc ctcgtcggac tcaccggctt cacccgcgcc ctcgccgcgg ccggcctgtc   2641 cgtcgcctcg gacgccaccg tggcctacct gcgcgcccctg cgcgagatcg acctcggcga   2701 ccgccgtcag gtgtactggg ccgggcgcgc caccctgtgc cacgaccccg acgacatccc    2761 ccgctacgac ctcgcgttcg agagctggtt cggcggaacg gcacccgacg tgacgtcgcc    2821 g                                                                    2822

<210> SEQ ID NO 7
<211> LENGTH: 465
<212> TYPE: PRT
<213> ORGANISM: Rhodococcus sp.
<220> FEATURE:
<221> NAME/KEY: misc_feature
<222> LOCATION: (556)..(556)
```

-continued

<223> OTHER INFORMATION: "n" may be a, c, g or t
<221> NAME/KEY: misc_feature
<222> LOCATION: (592)..(592)
<223> OTHER INFORMATION: "n" may be a, c, g or t
<221> NAME/KEY: misc_feature
<222> LOCATION: (896)..(896)
<223> OTHER INFORMATION: "n" may be a, c, g or t

<400> SEQUENCE: 7

```
Met Ser Ser Leu Thr Pro Pro Asn Ser Asn Gln Met Ser Ala Leu Asn
1               5                  10                  15

Asn His Phe Arg Phe Gly Leu Thr Thr Pro Glu Leu Glu Glu Phe Ala
            20                  25                  30

Pro Ala Leu Glu Ala Thr Leu Ala Ser Ser Glu Thr Val Glu Arg Leu
        35                  40                  45

Tyr Glu Arg Thr Ala Pro Glu Pro Pro Gln Arg Ser Trp Thr Ser Pro
50                  55                  60

Thr Ala Asp Glu Asn Pro Leu Ser Ala Trp Tyr Val Thr Thr Ser Ile
65                  70                  75                  80

Ser Glu Thr Asp Glu Gly Pro Leu Ala Gly Arg Thr Val Ala Val Lys
                85                  90                  95

Asp Asn Val Ala Val Ala Gly Val Pro Met Met Asn Gly Ser Arg Thr
            100                 105                 110

Val Glu Gly Phe Thr Pro Arg Tyr Asp Ala Thr Val Val Arg Arg Leu
        115                 120                 125

Leu Asp Ala Gly Ala Thr Ile Thr Gly Lys Ala Val Cys Glu Asp Leu
130                 135                 140

Cys Phe Ser Gly Ala Ser Phe Thr Ser His Pro Gln Pro Val Arg Asn
145                 150                 155                 160

Pro Trp Asp Glu Ser Arg Ile Thr Gly Gly Ser Ser Ser Gly Ser Gly
                165                 170                 175

Ala Leu Val Ala Ser Gly Gln Val Asp Met Ala Val Gly Gly Asp Gln
            180                 185                 190

Gly Gly Ser Ile Arg Ile Pro Ala Ala Phe Cys Gly Ile Val Gly His
        195                 200                 205

Lys Pro Thr His Gly Leu Val Pro Tyr Thr Gly Ala Phe Pro Ile Glu
210                 215                 220

Arg Thr Ile Asp His Leu Gly Pro Met Thr Arg Thr Val Ser Asp Ala
225                 230                 235                 240

Ala Ala Met Leu Thr Val Leu Ala Gly Thr Asp Gly Leu Asp Pro Arg
                245                 250                 255

Gln Thr His Arg Ile Glu Pro Val Asp Tyr Leu Ala Ala Leu Ala Glu
            260                 265                 270

Pro Ala Ser Gly Leu Arg Val Gly Val Val Thr Glu Gly Phe Asp Thr
        275                 280                 285

Pro Val Ser Asp Ala Ala Val Asp Asn Ala Val Arg Thr Ala Ile Gly
290                 295                 300

Val Leu Arg Ser Ala Gly Leu Thr Val Glu Glu Val Ser Ile Pro Trp
305                 310                 315                 320

His Leu Asp Ala Met Ala Val Trp Asn Val Ile Asp Arg Ala Asp Asp
                325                 330                 335

Glu Phe Glu Ala Phe Leu Leu Gln Val Leu Asp Glu Asn Ala Val Thr
            340                 345                 350

Ile Pro Glu Leu Gly Gln Val Arg Ala Gln Thr Pro Arg Ser Trp Cys
        355                 360                 365
```

-continued

```
Ser Pro Arg Thr Ala Pro Ala Arg Cys Thr Thr Pro Ser Asn Ala Ala
    370             375             380

Ala Cys Thr Thr Gly Ser Asn Thr Pro Thr Ser Arg Gly Lys Trp Arg
385             390             395                     400

Ser Cys Ala Ala Ala Ser Arg Ala Ser Thr Asn Thr Ser Arg Arg Arg
            405             410              415

Ser Pro Thr Pro Cys Arg Pro Cys Ala Gly Trp Thr Cys Ser Asn His
        420             425             430

Pro Gly Ser Arg Ser Arg Trp Thr Gly His Glu Arg Cys Gly Asn Ser
        435             440             445

Thr Ala Thr Cys Ser Thr Arg Arg Pro Arg Pro Arg Pro Ser Val Pro
    450             455             460

Ser
465
```

RHODOCOCCUS BACTERIUM, NITRILASE GENE, NITRYLHYDRATASE GENE AND AMIDASE GENE FROM *RHONDOCOCCUS* BACTERIUM, AND PROCESS FOR PRODUCING CARBOXYLIC ACIDS BY USING THEM

CROSS-REFERENCE TO RELATED APPLICATIONS

This application is based on the provisions of 35 U.S.C. Article 111(a) to claim the benefit of filing dates of U.S. provisional application Ser. No. 60/183,754 filed on Feb. 22, 2000 and U.S. provisional application Ser. No. 60/183,821 filed Feb. 22, 2000 under the provisions of 35 U.S.C. 111(b), pursuant to the provision of 35 U.S.C. Article 119(e) (i).

TECHNICAL FIELD

The present invention relates to a novel *Rhodococcus* bacterium and to a process for hydrolyzing a cyano group of a nitrile compound using a novel *Rhodococcus* bacterium to produce the corresponding carboxylic acid. The present invention also relates to a process of producing carboxylic acids, in particular cyano carboxylic acids using a transformant transformed with a plasmid containing a nitrilase gene, a nitrile hydratase gene, and an amidase gene derived from a *Rhodococcus* bacterium capable of exhibiting particularly excellent position selectivity for the cyano group of aromatic polynitrile compounds, to such a transformant, such a plasmid, to such genes, to a process of producing an enzyme using the transformant, and to enzymes obtained by the process. The carboxylic acids, in particular cyano carboxylic acids obtained by the present invention are useful as starting materials for the synthesis of drugs, agrochemicals, dyestuff and other chemicals.

BACKGROUND ART

Many studies have been made on the reaction of hydrolyzing a cyano group of a nitrile compound to obtain the corresponding carboxyl acids, because this is a simple and easy process for obtaining carboxylic acids.

With respect to the bioreaction of hydrolyzing only a part of the cyano groups of a polynitrile compound having a plurality of cyano groups in one molecule to obtain the corresponding cyano carboxylic acid, in particular, with respect to the process for obtaining aromatic cyano carboxylic acids by selectively hydrolyzing only a specific cyano group of an aromatic polynitrile compound, many reports have been published on the reaction utilizing the specificity to the reaction of the microorganism. For example, U.S. Pat. No. 4,629,700 discloses a process of producing cyanobenzoic acids from phthalonitriles using a *Rhodococcus* bacterium. Also, for example, European Patent 178,106 discloses a process for producing cyano carboxylic acids and cyano carboxylic acid amides by the selective hydrolysis of a cyano group from a polynitrile compound using four genera of gram positive bacteria including the genus *Rhodococcus*.

Selective hydrolysis reactions of a cyano group in a chemical synthesis are generally not suitable for the practical use because in order to perform the reaction, a complicated procedure, such as protection of a specific cyano group, is necessary.

Bioreactions are generally admitted to have high selectivity. However, when strictly inspected, they are in many cases accompanied by production of impurities due to side reaction. For example, according to the above-described process for producing a cyano benzoic acid from a phthalonitrile using a *Rhodococcus* bacterium, the selectivity is not 100%, but the reaction is accompanied by from 1.0% to a few % of by-products originating in the phthalonitrile. From the standpoint of the conversion from a starting material, this may be said to be an excellent process. However, in the synthesis of medicaments or fine chemicals, the behaviors of a slight amount of by-products greatly affect the capability or safety of a substance synthesized using a starting material containing the by-products. Therefore, the above-described selectivity is not sufficiently high for the starting material in this field.

In order to elevate the purity of the products, a method of obtaining a product and thereafter further purifying it may be considered. However, for example, various by-products produced in the process of biologically producing a cyano carboxylic acid from an aromatic polynitrile are very close to each other in the physical properties such as boiling point and hydrophobicity, and complete separation thereof cannot be attained by commonly used purification methods such as distillation, extraction, and salting out.

As such, in conventional processes for producing carboxylic acids by a hydrolysis reaction of a nitrile compound using microorganisms, the selectivity of the hydrolysis reaction itself is not high and the production of by-products is not sufficiently reduced.

An alternative method for producing carboxylic acids by the hydrolysis of a nitrile compound includes enzymatic reaction methods using nitrilase, or nitrile hydratase and amidase.

The nitrilase is an enzyme which catalyzes a reaction of converting a nitrile compound into a carboxylic acid and this is useful means for obtaining a carboxylic acid useful as a raw material for medical and agrochemical preparations. Examples of the microorganisms which produces this enzyme include *Fusarium solani* (see *Biochem. J.* 167, 685–692 (1977)), *Nocardia* sp. (see, *Int. J. Biochem.*, 17, 677–683 (1985)), *Arthrobacter* sp. (see, *Appl. Environ. Microbiol.*, 51, 302–306 (1986)), *Rhodococcus rhodochrous* J1 (see, *Eur. J. Biochem.*, 182, 349–356 (1989)), *Rhodococcus rhodochrous* K-22 (see, *J. Bacterio.*, 172, 4807–4815 (1990)), *Rhodococcus rhodochrous* PA-34 (see, *Appl. Microbiol. Biotechnol.*, 37, 184–190 (1992)) and *Rhodococcus* sp. ATCC39484 (see, *Biotechnol. Appl. Biochem.*, 15, 283–302 sp. (1992)).

From these microorganisms, nitrilase, nitrile hydratase, or amidase is produced. In order to use these enzymes in the genetic engineering, genes of some of these enzymes have been isolated and their primary structure has been determined. With respect to the nitrilase gene, genes from *Rhodococcus* bacteria are disclosed, for example, in JP-A-7-99980 (the term "JP-A" as used herein denotes an unexamined Japanese patent application, first publication) and JP-A-9-28382.

In recent years, attempts have been made to utilize the capability of converting a nitrile compound these microorganisms have. Particularly, for the production of compounds having a high added value, an enzyme having excellent steric selectivity or position selectivity is required. For example, JP-A-2-84198 discloses microorganisms for use in the production of an optically active α-substituted organic acid, JP-A-4-341185 discloses microorganisms for use in the production of an optically active 2-hydroxycarboxylic acid, and EPO433117 discloses microorganisms for use in the production of optically active ketoprofen.

Among these microorganisms, the *Rhodococcus* sp. ATCC39484 strain has been reported to have a capacity to hydrolyze aromatic polynitrile compounds having a plurality of nitrile groups with excellent position selectivity (see, U.S. Pat. No. 556,625). The compounds having a nitrile group and a carboxyl group in the molecule, which are produced by this selective nitrile degrading enzymatic system, are very effective as a synthesis block in the production of medical or agrochemical preparations. However, the nitrilase of this microorganism is relatively low in the activity on aromatic polynitrile compounds and for utilizing this property in industry, it is an essential matter to improve the productivity of the enzyme which catalyzes the reaction. However, the nitrilase gene of this microorganism, which is indispensable in the intended modification, has not yet been elucidated.

Nitrile hydratase and amidase are enzymes which catalyze the reactions of converting a nitrile compound to an amide and an amide to a carboxylic acid, respectively. By using nitrile hydratase and amidase, amides and carboxylic acids useful as starting materials for medicines, agrochemicals, etc. can be obtained from nitrile compounds. Methods for converting nitrile compounds to corresponding amides or carboxylic acids have been developed by utilizing biocatalysts, and many microorganisms having such catalytic activity have been reported (see, JP-B-56-17918 (the term "JP-B" as used herein means an examined Japanese patent application, second publication), JP-B-59-037951, JP-B-61-162193, JP-B-61-021519, JP-B-64-086889, JP-B-4-197189, JP-B-2-000470, EP0444640, etc.).

From these microorganisms, nitrile hydratase and amidase or nitrilase have been purified, and further, in order to utilize these genes in genetic engineering, the genes have been isolated and their primary structures have been determined. With respect to the nitrile hydratase gene, for example, genes derived from *Rhodococcus* bacteria are disclosed in U.S. Pat. No. 2,840,253 and EP0445646 (JP-A-40211379), genes derived from *Pseudomonas* bacteria are disclosed in JP-A-30251184, genes derived from *Rhizobium* bacteria are disclosed in JP-A-6-025296 and JP-A-6-303971. Also, with respect to the amidase gene, for example, genes derived from *Brevibacterium* bacteria and genes derived from *Rhodococcus* are disclosed in EP0433117. Further, genes derived from *Rhodococcus erythropolis* are reported in *Eur. J. Biochem.* 217(1), 327–336 (1993) and genes derived from *Pseudomonas* bacteria are reported in *FEBS Lett.* 367, 275–279 (1995).

Further, an invention relating to a recombinant plasmid containing both a nitrile hydratase gene and an amidase gene derived from *Rhodococcus* bacteria is disclosed in JP-A-5-068566.

In recent years, attempts have been made to utilize the capacity to convert a nitrile compound that these microorganisms have. Particularly, for the production of compounds having a high added value, an enzyme having excellent steric selectivity or position selectivity is required. For example, JP-A-2-84198 discloses microorganisms for use in the production of an optically active α-substituted organic acid, JP-A-4-341185 discloses microorganisms for use in the production of an optically active 2-hydroxycarboxylic acid, and EP0433117 discloses microorganisms for use in the production of optically active ketoprofen.

Among these microorganisms, the *Rhodococcus* sp. ATCC39484 strain has been reported to have a capacity to hydrolyze aromatic polynitrile compounds having a plurality of nitrile groups with excellent position selectivity (see, U.S. Pat. No. 556,625). The compounds having a cyano group and an amide group in the molecule or those compounds having a cyano group and a carboxyl group in the molecule, which are produced by this selective nitrile degrading enzymatic system, are very effective as a synthesis block in the production of medical or agrochemical preparations. However, the nitrilase of this microorganism is relatively low in the activity on aromatic polynitrile compounds and for utilizing this property in industry, it is an essential matter to improve the productivity of the enzyme which catalyzes the reaction. However, the related enzyme genes of this microorganism, which are indispensable in the intended modification, have not yet been elucidated for either nitrile hydratase and amidase.

DISCLOSURE OF THE INVENTION

In consideration of the above-described problems, an object of the present invention is to provide a process for producing carboxylic acid, in which the hydrolysis reaction is favored with a higher yield than those in conventional processes and reduced in the amount of by-products, and also to provide a process for producing cyano carboxylic acids, comprising selectively hydrolyzing only a specific cyano group of a polynitrile compound to produce the corresponding cyano carboxylic acid, in which the hydrolysis reaction is favored with a higher yield than those in conventional processes and a reduced amount of by-products, and a mutant microorganism which catalyzes the above-described reactions.

Another object of the present invention is to provide a novel nitrilase gene, a nitrile hydratase gene, and an amidase gene derived from a bacterium *Rhodococcus*. Still another object of the present invention is to provide a process for producing carboxylic acids from a nitrile compound, using a transformant transformed with a plasmid having incorporated therein these genes by using genetic engineering techniques. Yet another object of the present invention is to provide such a transformant, such a plasmid, such genes, a process of producing an enzyme using the transformant, and an enzyme obtained by the process.

The present inventors have made extensive investigations to substantially reduce the by-products due to side reactions in the conventional hydrolysis reactions of a cyano group by microorganisms. In particular, the by-products produced in various known techniques for producing cyanobenzoic acids from phthalonitriles were precisely analyzed, and as a result it has been found that the by-products produced in this reaction are mainly cyanobenzamide and phthalic acid monoamide further hydrolyzed from the cyanobenzamide. Also, it has been found that when a microorganism defective or reduced in the activity of converting nitrile into amide is used in the reaction, those by-products can be greatly decreased.

For example, from the report by Kobayashi et al. (Nippon Nogeikagaku Kaishi (Japan Society for Bioscience, Biotechnology, and Agrochemistry), Vol. 71, No. 12 (1997)), and the like, it is known that two routes are present for the reaction by a microorganism to hydrolyze a cyano group of a nitrile compound into a carboxylic acid, (1) a one-stage reaction route by a nitrilase and (2) a two-stage reaction route of once passing through an amide form by two enzymes of nitrile hydratase and amidase.

The present inventors have particularly studied the reaction route used in the conversion from a polynitrile compound into a cyano carboxylic acid by *Rhodococcus* sp. ATCC39484, which is a known nitrile converting bacterium. This strain is confirmed to cause a reaction in a cell suspension to thereby produce a cyanobenzoic acid as a main product from phthalonitrile and at the same time produce cyanobenzamide and phthalic acid monoamide as by-products. This was further studied and as a result it is estimated that the above-described two kinds of routes both competitively function in the hydrolysis of phthalonitrile by this microorganism. From these, the present inventors have come to a conclusion that although the activity of the amide route has been considered useful for the production of a carboxylic acid by the hydrolysis of nitrile, by rather making the activity defective or reduced, the by-products in question, specifically, cyanobenzamide and phthalic acid monoamide hydrolyzed from the cyanobenzamide, can be removed or reduced at the same time.

From a parent strain ATCC39484, variant strain groups were formed using NTG (N-methyl-N'-nitro-N-nitrosoguanidine) in the ordinary manner. Based on the assumption that the two-stage route passing through an amide form described above is under a series of controls, these variant groups were subjected to screening having as a target the inability to grow using benzamide as a sole carbon/nitrogen source. As a result, many non-growing strains were acquired and actually subjected to the above-described reaction. Then, a microorganism capable of extremely reducing the production of cyanobenzamide and phthalic acid monoamide in the reaction with phthalonitrile was acquired and designated as SD826 strain. This acquisition has led to the accomplishment of the present invention.

An embodiment of the present invention provides a process for producing carboxylic acids, comprising converting at least one cyano group of a nitrile compound into a carboxyl group using a microorganism, wherein a variant microorganism defective or reduced in the activity to convert a cyano group into an amide group is used.

The variant microorganism may be a variant strain of a bacterium belonging to the genus *Rhodococcus*. Further, the variant strain of a *Rhodococcus* bacterium may be a variant strain of a parent strain *Rhodococcus* sp. ATCC39484. Further, in a preferred embodiment, the variant strain of a parent strain *Rhodococcus* sp. ATCC39484 may be *Rhodococcus* sp. SD826 (FERM BP-7305).

In the above process, the nitrile compound may be a polynitrile compound having a plurality of cyano groups in the molecule and the carboxylic acid may be a cyano carboxylic acid. In a preferred embodiment, the polynitrile compound is an aromatic polynitrile compound and the cyano carboxylic acid is an aromatic cyano carboxylic acid. More preferably, the aromatic polynitrile compound is o-phthalonitrile, isophthalonitrile, or terephthalonitrile, and the aromatic cyano carboxylic acid is o-cyanobenzoic acid, m-cyanobenzoic acid, or p-cyanobenzoic acid.

Another embodiment of the present invention provides a variant microorganism having an activity to covert a cyano group into a carboxyl group and being defective or reduced in the activity of converting a cyano group into an amide group. The variant may be a variant strain of a microorganism belonging to the genus *Rhodococcus*. In a preferred embodiment, the variant microorganism is a variant strain of *Rhodococcus* sp. ATCC39484.

Another embodiment of the present invention provides a *Rhodococcus* sp. SD826 (FERM BP-7305) strain. The *Rhodococcus* sp. SD826 has been deposited on Oct. 12, 1999 at National Institute of Bioscience and Human-Technology, Agency of Industrial Science and Technology, Ministry of International Trade and Industry (1–3, Higashi 1-chome Tsukuba-shi Ibaraki-ken, Japan)(Accession Number: FERM BP-7305).

Another embodiment of the present invention provides a process for producing carboxylic acids, comprising converting a cyano group of a nitrile compound into a carboxyl group using a transformant transformed with a plasmid containing a nitrilase gene derived from *Rhodococcus* bacterium consisting of a DNA sequence encoding the amino acid sequence shown by SEQ ID NO 2 of the sequence list.

Another embodiment of the present invention provides a process for producing carboxylic acids, comprising converting a cyano group of a nitrile compound into a carboxyl group using a transformant transformed with a plasmid containing a nitrilase gene derived from *Rhodococcus* bacterium consisting of a DNA sequence shown by SEQ ID NO 1 in the sequence list.

Another embodiment of the present invention provides a process for producing cyano carboxylic acids, comprising converting at least one nitrile group of a polynitrile compound into a carboxyl group using the above-described transformant.

In these production processes, the polynitrile compound may be an aromatic polynitrile compound. Preferably, the aromatic polynitrile compound may be phthalonitrile, isophthalonitrile, or terephthalonitrile, and the cyano carboxylic acid may be o-cyanobenzoic acid, m-cyanobenzoic acid or p-cyanobenzoic acid.

Another embodiment of the present invention provides a transformant transformed with a plasmid containing a nitrilase gene derived from *Rhodococcus* bacterium consisting of a DNA sequence encoding the amino acid sequence shown by SEQ ID NO 2 of the sequence list, for use in the process described above.

Another embodiment of the present invention provides a transformant transformed with a plasmid containing a nitrilase gene derived from *Rhodococcus* bacterium consisting of a DNA sequence shown by SEQ ID NO 1 of the sequence list, for use in the above-described production processes.

Another embodiment of the present invention provides a plasmid containing a nitrilase gene derived from *Rhodococcus* bacterium consisting of a DNA sequence encoding the amino acid sequence shown by SEQ ID NO 2 of the sequence list, for use in the preparation of the above-described transformant.

Another embodiment of the present invention provides a plasmid containing a nitrilase gene derived from *Rhodococcus* bacterium consisting of a DNA sequence shown by SEQ ID NO 1 of the sequence list, for use in the preparation of the above-described transformant.

Another embodiment of the present invention provides a nitrilase gene derived from *Rhodococcus* bacterium consisting of a DNA sequence encoding the amino acid sequence shown by SEQ ID NO 2 of the sequence list.

Another embodiment of the present invention provides a nitrilase gene derived from *Rhodococcus* bacterium consisting of a DNA sequence shown by SEQ ID NO 1 of the sequence list.

The *Rhodococcus* bacterium may be a *Rhodococcus* sp. ATCC39484 strain.

Another embodiment of the present invention provides a process for producing nitrilase, comprising culturing the above-described transformant in a culture medium and collecting nitrilase from the culture.

Another embodiment of the present invention provides nitrilase prepared by the above-described process.

Another embodiment of the present invention provides a process for producing amide compounds, comprising converting a cyano group of a nitrile compound into an amide group using a transformant transformed with a plasmid containing a nitrile hydratase gene derived from *Rhodococcus* bacterium consisting of a DNA sequence encoding the amino acid sequences shown by SEQ ID NOs 4 and 5 of the sequence list.

Another embodiment of the present invention provides a process for producing amide compounds, comprising converting a cyano group of a nitrile compound into an amide group using a transformant transformed with a plasmid containing a nitrile hydratase gene derived from *Rhodococcus* bacterium consisting of a DNA sequence shown by SEQ ID NO 3 in the sequence list.

Another embodiment of the present invention provides a process for producing carboxylic acids, comprising converting an amide group of an amide compound into a carboxyl group using a transformant transformed with a plasmid containing an amidase gene derived from *Rhodococcus* bacterium consisting of a DNA sequence encoding the amino acid sequence shown by SEQ ID NO 7 of the sequence list.

Another embodiment of the present invention provides a process for producing carboxylic acids, comprising converting an amide group of an amide compound into a carboxyl group using a transformant transformed with a plasmid containing an amidase gene derived from *Rhodococcus* bacterium consisting of a DNA sequence shown by SEQ ID NO 6 of the sequence list.

Another embodiment of the present invention provides a process for producing carboxylic acids, comprising converting a cyano group of a nitrile compound into a carboxyl group using a transformant transformed with a plasmid containing both a nitrile hydratase gene derived from *Rhodococcus* bacterium consisting of a DNA sequence encoding the amino acid sequences shown by SEQ ID NOs 4 and/or 5 of the sequence list and an amidase gene derived from *Rhodococcus* bacterium consisting of a DNA sequence encoding the amino acid sequence shown by SEQ ID NO 7 of the sequence list.

Another embodiment of the present invention provides a process for producing carboxylic acids, comprising converting a cyano group of a nitrile compound into a carboxyl group using a transformant transformed with a plasmid containing both a nitrile hydratase gene derived from *Rhodococcus* bacterium consisting of a DNA sequence shown by SEQ ID NO 3 of the sequence list and an amidase gene derived from *Rhodococcus* bacterium consisting of a DNA sequence shown by SEQ ID NO 6 of the sequence list.

Another embodiment of the present invention provides a process for producing amide compounds, wherein the nitrile is orthophthalonitrile, isophthalonitrile, or terephthalonitrile, and the amide compound is o-cyanobenzamide, m-cyanobenzamide, or p-cyanobenzamide.

In the above-described production, the amide compound may be o-cyanobenzamide, m-cyanobenzamide, or p-cyanobenzamide and the carboxylic acid may be o-, m-, or p-cyanobenzoic acid. The nitrile may be orthophthalonitrile, isophthalonitrile, or terephthalonitrile, and the carboxylic acid may be o-, m-, or p-cyanobenzoic acid.

Another embodiment of the present invention provides a transformant transformed with a plasmid containing a nitrile hydratase gene derived from *Rhodococcus* bacterium consisting of a DNA sequence encoding the amino acid sequences shown by SEQ ID NOs 4 and/or 5 of the sequence list, for use in the above-described process.

Another embodiment of the present invention provides a transformant transformed with a plasmid containing a nitrile hydratase gene derived from *Rhodococcus* bacterium consisting of a DNA sequence shown by SEQ ID NO 3 of the sequence list, for use in the above-described process.

Another embodiment of the present invention provides a transformant transformed with a plasmid containing an amidase gene derived from *Rhodococcus* bacterium consisting of a DNA sequence encoding the amino acid sequences shown by SEQ ID NO 7 of the sequence list, for use in the above-described process.

Another embodiment of the present invention provides a transformant transformed with a plasmid containing an amidase gene derived from *Rhodococcus* bacterium consisting of a DNA sequence shown by SEQ ID NO 6 of the sequence list, for use in the above-described process.

Another embodiment of the present invention provides a transformant transformed with a plasmid containing both a nitrile hydratase gene derived from *Rhodococcus* bacterium consisting of a DNA sequence encoding the amino acid sequences shown by SEQ ID NOs 4 and 5 of the sequence list and an amidase gene derived from *Rhodococcus* bacterium consisting of a DNA sequence encoding the amino acid sequence shown by SEQ ID NO 7 of the sequence list, for use in the above-described process.

Another embodiment of the present invention provides a transformant transformed with a plasmid containing both a nitrile hydratase gene derived from *Rhodococcus* bacterium consisting of a DNA sequence shown by SEQ ID NO 3 of the sequence list and an amidase gene derived from *Rhodococcus* bacterium consisting of a DNA sequence shown by SEQ ID NO 6 of the sequence list, for use in the above-described process.

Another embodiment of the present invention provides a plasmid containing a nitrile hydratase gene derived from *Rhodococcus* bacterium consisting of a DNA sequence encoding the amino acid sequences shown by SEQ ID NOs 4 and 5 of the sequence list, for use in the preparation of the above-described transformant.

Another embodiment of the present invention provides a plasmid containing a nitrile hydratase gene derived from *Rhodococcus* bacterium consisting of a DNA sequence shown by SEQ ID NO 3 of the sequence list, for use in the preparation of the above-described transformant.

Another embodiment of the present invention provides a plasmid containing an amidase gene derived from *Rhodococcus* bacterium consisting of a DNA sequence encoding the amino acid sequence shown by SEQ ID NO 7 of the sequence list, for use in the preparation of the above-described transformant.

Another embodiment of the present invention provides a plasmid containing an amidase gene derived from *Rhodococcus* bacterium consisting of a DNA sequence shown by SEQ ID NO 6 of the sequence list, for use in the preparation of the above-described transformant.

Another embodiment of the present invention provides a plasmid containing both a nitrile hydratase gene derived from *Rhodococcus* bacterium consisting of a DNA sequence encoding the amino acid sequences shown by SEQ ID NOs 4 and/or 5 of the sequence list and an amidase gene derived from *Rhodococcus* bacterium consisting of a DNA sequence encoding the amino acid sequence shown by SEQ ID NO 7 of the sequence list, for use in the preparation of the above-described transformant.

Another embodiment of the present invention provides a plasmid containing both a nitrile hydratase gene derived from *Rhodococcus* bacterium consisting of a DNA sequence shown by SEQ ID NO 3 of the sequence list and an amidase gene derived from *Rhodococcus* bacterium consisting of a DNA sequence shown by SEQ ID NO 6 of the sequence list, for use in the preparation of the above-described transformant.

Another embodiment of the present invention provides a nitrile hydratase gene derived from *Rhodococcus* bacterium consisting of a DNA sequence encoding the amino acid sequence shown by SEQ ID NOs 4 and 5 of the sequence list.

Another embodiment of the present invention provides a nitrile hydratase gene derived from *Rhodococcus* bacterium consisting of a DNA sequence shown by SEQ ID NO 3 of the sequence list.

The *Rhodococcus* bacterium may be a *Rhodococcus* sp. ATCC39484 strain.

Another embodiment of the present invention provides an amidase gene derived from *Rhodococcus* bacterium consisting of a DNA sequence encoding the amino acid sequence shown by SEQ ID NO 7 of the sequence list.

Another embodiment of the present invention provides an amidase gene derived from *Rhodococcus* bacterium consisting of a DNA sequence shown by SEQ ID NO 6 of the sequence list.

The *Rhodococcus* bacterium may be a *Rhodococcus* sp. ATCC39484 strain.

Another embodiment of the present invention provides a process for producing nitrile hydratase, comprising culturing the above-described transformant in a culture medium and collecting nitrile hydratase from the culture.

Another embodiment of the present invention provides a process for producing amidase, comprising culturing the above-described transformant in a culture medium and collecting amidase from the culture.

Another embodiment of the present invention provides a process for producing nitrile hydratase and/or amidase, comprising culturing the above-described transformant in a culture medium and collecting nitrile hydratase and/or amidase from the culture.

Another embodiment of the present invention provides nitrile hydratase prepared by the above production process.

Another embodiment of the present invention provides amidase prepared by the above-described process.

Another embodiment of the present invention provides nitrile hydratase and/or amidase prepared by the above-described process.

According to the present invention, high purity carboxylic acids can be simply and easily obtained from nitrile compounds as starting materials using a novel variant belonging to the genus *Rhodococcus*. Also, high purity cyanocarboxylic acids can be simply and easily obtained from polynitrile compounds, particularly aromatic polynitrile compounds as starting materials.

Further, the present invention provides a nitrilase gene, a nitrile hydratase gene and an amidase gene derived from *Rhodococcus* bacteria capable of exhibiting particularly excellent position selectivity for the cyano group of aromatic polynitrile compounds. The DNA sequences of these genes derived from the *Rhodococcus* bacterium are indispensable for efficient production of nitrile hydratase and amidase using genetic engineering techniques and improvement of enzymes using protein engineering techniques. As expected, the enzymes thus obtained are applicable to the industrial production of useful compounds.

PREFERRED EMBODIMENTS OF THE INVENTION

Figure 1:
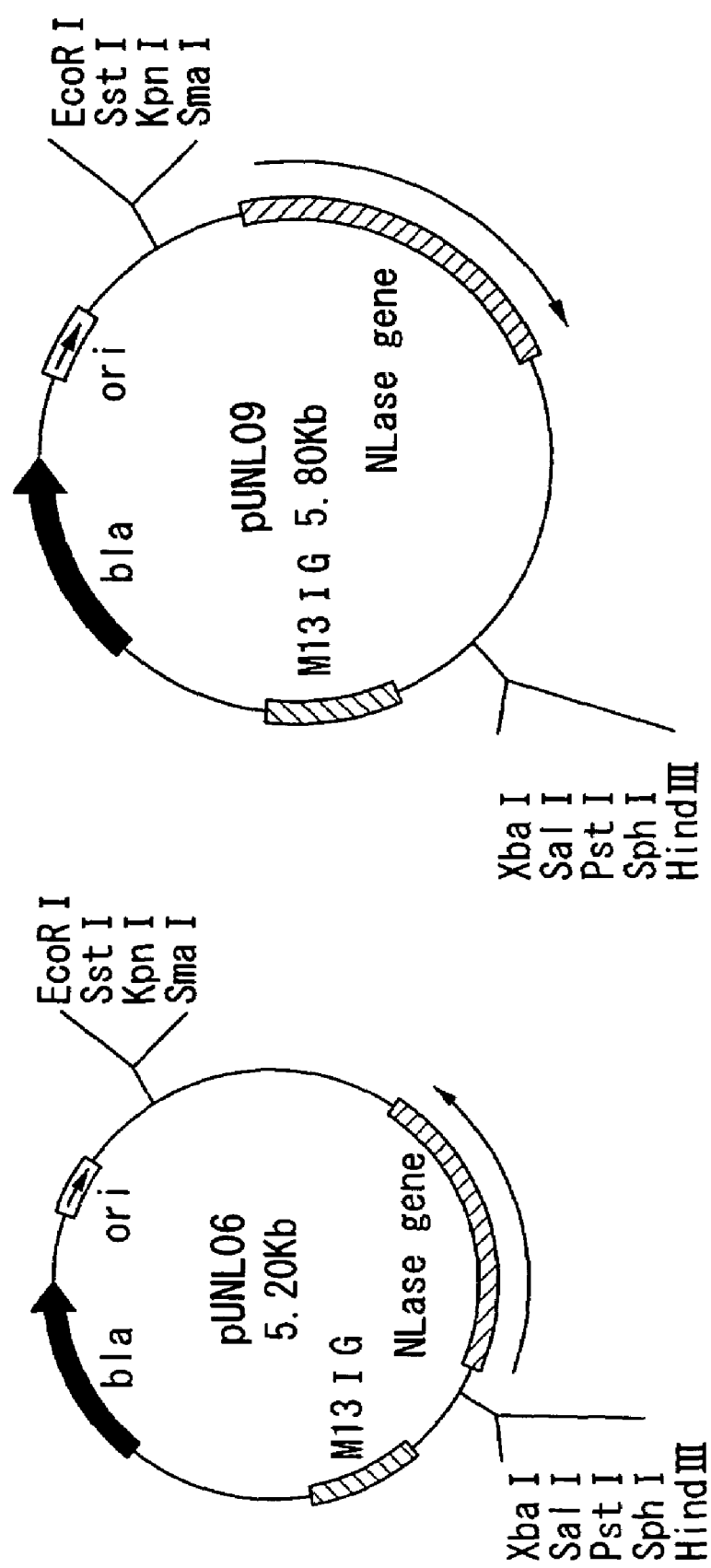
FIG. 1 is a schematic diagram illustrating the structure of a plasmid prepared from a positive clone obtained by the colony hybridization (Example 4).

1. Variant Microorganisms for Preparing Carboxylic Acids

As the parent strain used in the present invention for producing a variant microorganism defective or reduced in the activity of hydrolyzing a cyano group into an amide group, various generally known microorganisms having an activity to hydrolyze a cyano group of a nitrile compound may be used. In particular, microorganisms which have a nitrilase activity and allow a nitrile compound to undergo a carboxylic acid-generating reaction by hydration such that the by-products are an amide form, may be used. Examples of the microorganisms known to have an activity of hydrolyzing nitrile include the microorganisms belonging to genera such as *Rhodococcus, Rhodotorulla, Fusarium, Pseudomonas, Acinetobacter, Bacillus, Brevibacterium, Klebsiella, Micrococcus, Burkholderia, Corynebacterium, Noccardia, Aeromonas, Agrobacterium, Achromobacter, Aspergillus* and *Rhizobium*.

For example, the *Rhodococcus* sp. ATCC39484 strain is cultured by a commonly known method for culturing microorganisms, and a generally known variation inductive compound or an ultraviolet ray is provided to act on the cells obtained to prepare a variant microorganism group. Examples of the variation inductive compound include alkylating agents such as NTG (N-methyl-N'-nitro-N-nitrosoguanidine) and EMS (ethyl methanesulfonate), base analogs such as 5-bromouracil, and intercalation agents such as azaserine and acridine orange.

From the variant microorganism group prepared, variant strains reduced or defective in the activity of producing an amide compound from a nitrile compound are selected. The fact that the variant strain is reduced or defective in the activity of producing an amide compound may be demonstrated as follows. Culture cells of the variant microorganism strain are allowed to act on a nitrile compound, the product obtained is analyzed by a method of analysis such as HPLC, and the state how the corresponding carboxylic acid amide form is produced accompanying the degradation of the nitrile compound is observed.

At this time, in order to effectively concentrate the objective variant strains from a huge variant microorganism group, based on the assumption that the two-stage route passing through the amide form is subject to a series of control, the inventors considered using the loss or reduction of the activity of growth by assimilating an amide compound which can nourish and grow the parent strain microorganism, for example, benzamide or the like when ATCC39484 is the parent strain, as an index for the absence or reduction of a series of the reaction route to a carboxylic acid through an amide compound. By various methods using this index, an efficient concentration of the objective variant microorganism form a variant microorganism group can be realized.

The term "the loss or reduction of the activity of growth by assimilating an amide compound" as used in the present invention means that in the culture using the same amide compound as a nutrient source, the doubling time of the microorganisms is almost 2 times longer than that of the parent strain, or that the microorganisms cannot grow at all. For example, a variant microorganism group is spread on an ordinary nutritive agar culture medium, for example, LB agar culture medium, and then, the colonies formed are individually transplanted on an agar culture medium which contains benzamide as a sole carbon/nitrogen source, and by visually observing the presence or absence of the growth, the variant strains changed in the activity to assimilate benzamide can be detected. Also, by applying what is termed the penicillin screening method, the variant microorganisms defective or reduced in the activity of growing using benzamide can be concentrated. More specifically, a drug which acts on microorganisms in the process of their fission and growth and kills the microorganisms, for example, penicillin, is added to the culture medium using benzamide as a sole carbon/nitrogen source, and a variant microorganism group is inoculated thereon and cultured, where the strains capable of growing well with benzamide are killed and the strains defective or reduced in the activity of assimilating benzamide and growling are concentrated. Thus, a concentrated group of variant microorganisms is obtained.

The cultured cells of each variant microorganism are allowed to act on a nitrile compound, for example, phthalonitrile when the parent strain is ATCC39484, and the product obtained is analyzed by a method of analysis such as HPLC to search for the strains reduced in the accumulation of the carboxylic acid amide form. In the group of variant microorganisms thus concentrated, the strain reduced in the accumulation of the carboxylic acid amide form is found together with strains increased in the accumulation.

One example of the variant strain thus created is *Rhodococcus* sp. SD826. The *Rhodococcus* sp. SD826 is a strain created by the present inventors from *Rhodococcus* sp. ATCC39484 (divided from American Type Culture Collection in U.S.A.) which is a known microorganism, and this new variant strain has been deposited at National Institute of Bioscience and Human-Technology, Agency of Industrial Science and Technology, Ministry of International Trade and Industry, Japan, as FERM BP-7305.

For example, the variant microorganism strain reduced or defective in the ability to produce amide compounds applied to the present invention may be acquired by destroying or deleting enzymes or factors regulating the enzymes participating in the production of amide compounds and regions of gene encoding these using genetic engineering techniques. More specifically, it is realized as follows. Related genes of enzymes contributing to the reaction are isolated and analyzed, a gene fragment having incorporated therein is introduced, a sequence having homology to the base sequence is introduced into a microorganism, and homologous recombination between enzyme-related genes on the chromosome is induced to cause insertion or deletion of the base sequence.

The microorganisms which are applied to the present invention are those microorganisms which are reduced or defective in the ability to produce an amide compound. The modification operation may affect other properties of the microorganism, in particular the ability to produce carboxylic acids which would be considered to be closely related to each other. However, according to the object of the present invention, it may be sufficient that the production of amide compounds be relatively reduced as compared with the resulting carboxylic acid. Although it is desirable that such a modification will cause no decrease in the ability of a variant strain to produce carboxylic acids as compared with that of the parent strain before the modification, the ability to produce carboxylic acids may vary within the ranges where the production of amide compounds is relatively decreased.

The reaction of the present invention uses the thus-created variant microorganism and can be performed in the same manner as in the conversion reaction using a general microorganism in an ordinary carboxylic acid-generating reaction by a microorganism having the activity of hydrolyzing a cyano group. For example, the SD826 strain is cultured in a nutritive culture medium of 1% peptone or the like at a temperature of from 20 to 40° C., preferably from 25 to 30° C., for about 24 hours. To the resulting culture, a nitrile compound is added in an amount of from 1 ppm to 50%, preferably from 10 ppm to 10%, and then the solution is continuously stirred at the temperature mentioned above for from 1 to 200 hours, and thereby the reaction is carried out. The entire amount of the added nitrile compound is not be dissolved. However, a solvent, a surfactant, or the like which improves the solubility or dispersibility in the reaction solution may be added. In proportion with the amount of the nitrile compound consumed as the reaction proceeds, a nitrile compound may be added continuously or intermittently. At this time, the concentration of the nitrile compound in the reaction solution is not limited to the above-described range.

Examples of the carbon source which can be used in the culture medium for culturing microorganisms include saccharides such as glucose, sucrose, fructose and molasses, organic materials such as ethanol, acetic acid, citric acid, succinic acid, lactic acid, benzoic acid and fatty acid, alkali metal salts thereof, aliphatic hydrocarbons such as n-paraffin, aromatic hydrocarbons, and naturally occurring organic materials such as peptone, meat extract, fish extract, soybean powder and bran. These are used individually or in combination usually in a concentration of from 0.01 to 30%, preferably on the order of from 0.1 to 10%.

Examples of the nitrogen source which can be used in the culture medium for culturing microorganisms include inorganic nitrogen compounds such as ammonium sulfate, ammonium phosphate, sodium nitrate and potassium nitrate, nitrogen-containing organic materials such as urea and uric acid, and naturally occurring organic materials such as peptone, meat extract, fish extract and soybean powder. These are used individually or in combination usually in a concentration of from 0.01 to 30%, preferably from 0.1 to 10%. These starting materials for the reaction, of which cyano group is hydrolyzed by the strain into a carboxyl acid, are preferably added in advance during the culture, so that ammonium ion isolated by the hydrolysis with the progress of the reaction can serve as the nitrogen source for microorganisms.

Furthermore, in order to improve the growth of the cells, a phosphate such as potassium dihydrogenphosphate or metal salt such as magnesium sulfate, ferrous sulfate, calcium acetate, manganese chloride, copper sulfate, zinc sulfate, cobalt sulfate and nickel sulfate, may be added, if desired. The concentration in this addition varies depending on the culture conditions. However, it is usually from 0.01 to 5% for the phosphate, from 10 ppm to 1% for the magnesium salt, and approximately from 0.1 to 1,000 ppm for other compounds. In addition, depending on the culture medium selected, a source for supplying vitamins, amino acid, nucleic acid or the like, such as yeast extract, casamino acid, and yeast nucleic acid, may be added in an amount of approximately from 1 to 100 ppm, so that the growth of cells can be improved.

In order to improve the reactivity of cells with the cyano group, a nitrile compound such as benzonitrile is preferably added during the culture in an amount of from 10 ppm to 1% as a source for inducing a cyano group hydrolase. Furthermore, a nitrile compound which can serve both as a starting material for the reaction and an inducing source is preferably added during the culture.

In using any ingredient, the pH of the culture medium is preferably adjusted to from 5 to 9, more preferably from 6 to 8. Also, the reaction is preferably performed after collecting the microorganism cells previously cultured in the medium described above from the culture solution by centrifugation or filtration through a membrane and re-suspending them in water containing a nitrile compound as a reaction starting material, in a physiological saline, or in a buffer solution which is adjusted to have the same pH as the culture medium and comprises phosphoric acid, acetic acid, boric acid, tris(hydroxymethyl)aminomethane, or a salt thereof, because the impurities in the reaction solution can be reduced and afterward the product can be easily collected. The pH can be usually maintained during the reaction when a buffer solution having sufficiently high concentration is used. However, in the case where the pH departs from the above-described range with the progress of the reaction, the pH is preferably appropriately adjusted using sodium hydroxide, ammonia or the like.

The cyano carboxylic acid produced in the reaction solution is collected by a commonly used method such as centrifugation, filtration through a membrane, drying under reduced pressure, distillation, extraction with a solvent, salting out, ion exchange, and various kinds of chromatography. The collecting method is selected according to the status of the cyano carboxylic acid in the reaction solution. Most simply and easily, the cyano carboxylic acid is precipitated by adjusting the reaction solution to be acidic, and the precipitate is centrifuged or filtered to recover the cyano carboxylic acid. In the case where the reaction product is obtained as an aqueous solution, the microorganism cells are preferably removed by centrifugation, filtration through a membrane, or the like under the condition that the product is in the dissolved state. In the case where the reaction product is obtained as a solid and when the crystal is sufficiently large, the product may be collected using a mesh formed of stainless steel, nylon, or the like. When the crystal is small and cannot be fractionated from microorganisms, a method of once forming the reaction product into an aqueous solution by setting a condition where the solid can dissolve, for example, an alkali condition, removing the cells by centrifugation, filtration through a membrane or the like, recovering the condition, re-precipitating the solid, and collecting the reaction product, is preferably used. However, this is not an exclusive method if the microorganisms can be removed by means of ordinary art, such as direct distillation of the reaction solution.

Depending on the properties of the reaction product, the product may accumulate in the reaction solution to decrease the reaction rate. In this case, a method of adding water, physiological saline, or a reaction buffer solution to the reaction solution and continuously diluting the reaction solution according to the concentration of the product is suitably used. Also, the reaction rate can be recovered by collecting the cells at the time when the reaction rate has decreased, recovering the supernatant as a product solution, and returning the collected cells to the solution or suspension containing the reaction starting material. These methods each may be repeated on any number of occasions as long as the microorganisms maintain the activity of hydrolyzing nitrile.

The present invention may also be similarly performed even using a cell-free extract of the microorganisms applied to the present invention or using an ingredient which catalyzes the above-described reaction and which is concentrated or extracted from the cell-free extract. Furthermore, the present invention may be achieved by immobilizing a microorganism which can be applied to the present invention, or an extract solution or extracted ingredient thereof to a sparingly soluble supporter and bringing this immobilized matter into contact with a starting material solution. Examples of the supporter which can be used for the immobilization include compounds capable of forming a sparingly water-soluble solid containing the microorganism or an extracted ingredient thereof, such as polyacrylamide, polyvinyl alcohol, poly-N-vinylformamide, polyallylamine, polyethyleneimine, methyl cellulose, glucomannan, alginate, carrageenan, and a polymer or cross-linked product thereof. These compounds may be used individually or in combination. In addition, those obtained by bearing the microorganism or an extract solution or extracted ingredient thereof on a material previously formed as a solid, such as activated carbon, porous ceramic, glass fiber, porous polymer compact, and nitrocellulose membrane may be used.

According to the process of the present invention, the specificity of the substrate used for the hydrolysis reaction of cyano groups is broad, the object includes various commonly known nitrile compounds such as aliphatic nitrile, aromatic nitrile, and heterocyclic nitrile, and the corresponding carboxylic acid can be obtained with high selectivity.

Examples of the aliphatic nitrile include acetonitrile, propionitrile, n-butyronitrile, isobutyronitrile, n-valeronitrile, isovaleronitrile, capronitrile, malononitrile, glucononitrile, adiponitrile, succinonitrile, acrylonitrile and methacrylonitrile.

Examples of the aromatic nitrile include benzonitrile, terephthalonitrile, orthophthalonitrile, tolunitrile, isophthalonitrile and substitution products of these aromatic nitrile compounds, such as chlorinated product, fluorinated product, nitrated product and aminated product.

Examples of the heterocyclic nitrile include 3-cyanopyridine, 4-cyanopyridine and cyanoindoles.

Also, according to the present invention, the object is preferably a polynitrile compound having a plurality of cyano groups in one molecule among the compounds described defective or reduced in the above and the corresponding cyano carboxylic acid can be obtained with high selectivity. Examples of the polynitrile compound include aliphatic nitriles such as malononitrile, succinonitrile, adiponitrile and glucononitrile, aromatic nitrites such as orthophthalonitrile, terephthalonitrile and isophthalonitrile and substitution products of these aromatic nitrile compounds such as chlorinated product, fluorinated product, nitrated product and aminated product.

According to the process of the present invention, carboxylic acids reduced in the amount of by-products can be obtained, specifically, so as to contain the by-products originating in the starting material nitrile compound in a total amount of 0.5 (mol)% or less in the product carboxylic acid. In recent years, there is a great concern about the effects of trace chemical substances on human bodies and therefore, the present invention is made based on the concept that the substantial reduction of side reactions in the chemical reaction and high-purity chemicals obtained by such a reaction can create new possibilities in industry.

In the process of the present invention, the production route of a carboxylic acid through an amide is fundamentally defective or reduced and therefore amide-form impurities ascribable to the partial hydrolysis of nitrile, and derivatives thereof, are not produced. The carboxylic acids obtained by the present invention are suitable as a starting material for the synthesis in the field where high purity is particularly required, for example, in the field of medicaments or fine chemicals.

2. Nitrilase Gene Derived from *Rhodococcus* Bacteria

The method for determining the DNA sequence of the nitrilase gene of *Rhodococcus* sp. is described below. The chromosomal DNA, for example, of the *Rhodococcus* sp. ATCC39484 strain can be prepared by applying the method of Saito et al. (see, *Biochem. Biophys. Acta.,* 72, 619 (1963)). The chromosomal DNA library for use in the cloning of the gene can be manufactured using, for example, a plasmid vector pUC18. The cloning of the nitrilase gene can be performed using, for example, the polymerase chain reaction (PCR) by Saiki et al. (see, *Science* 230, 1350 (1985)). At this time, a universal primer (forward or reverse) is used as one primer in PCR and for another primer, an appropriate sequence is selected from the DNA sequence coding for an enzyme N terminal sequence. By combining these primers, an anchor PCR is performed using the chromosomal DNA library as a template and thereby the coding sequence fragment of the objective enzyme can be obtained. By using the nitrilase coding sequence DNA partial fragment as a probe for the screening of all gene regions, a recombinant DNA containing a nitrilase gene can be obtained from the chromosomal DNA library of the *Rhodococcus* sp. ATCC39484 strain. The DNA sequence of the nitrilase coding sequence fragment can be determined using known method such as the dideoxy method described by Sanger et al. (see, *Proc. Natl. Acad. Sci. U.S.A.,* 74, 5463 (1997)).

In order to produce a nitrilase enzyme using the thus-obtained enzyme structural gene, the enzyme structural gene is ligated with an appropriate expression vector, for example, downstream from the lac promoter of pUC 18. Using the thus-obtained plasmid, a host such as *Escherichia coli* JM101 is transformed. By culturing the obtained transformant, the objective nitrilase is produced in a very large amount within the host cells. The intact nitrilase cells may be used for the conversion reaction but a cell-free extract or purified enzyme obtained from the extract may also be used.

In order for enzyme genes derived from different microorganisms to be expressed in a host microorganism in a manner such that it actually functions therein, it is well known that various requirements must be satisfied, for example, that the gene is actually retained and divided in the host microorganism, that the gene is transcribed by the transcription function of the host, that the transcribed information is translated into a protein, that the polypeptide produced by the translation is folded into a higher dimensional structure so that it can have a function, that an enzyme is secreted in the same manner as in the donor microorganism so that the enzyme can contact a substrate, or if the enzyme is an intracellular enzyme, that the host microorganism has a permeation/transportation system similar to those of the donor microorganism, and so on. Further, in order for the expression to be in some degree useful for industrial application, each of the requirements must be satisfied at high levels. To solve these problems, usually, operations such as analysis and modification of regulating regions, e.g., promoters, adaptation of transcription/expression system and various cofactors to the body of the target gene by constructing a complicated shuttle vector and returning a cloned gene to the donor microorganism and the like become necessary. These methods have the problems that it is difficult to obtain information on the target of analysis and to modify the method of modification for the regulating mechanism, which must rely on a trial and error method, and that they are limited by the ability of the donor in performing the expression by returning the cloned gene to the donor. As far as the present inventors are aware, although some cases exist where the expression of nitrilase from a different microorganism has been confirmed, no case is known where a nitrilase gene is obtained which catalyzes selective hydrolysis of polynitrile and which can exhibit high activity far exceeding the ability of the donor microorganism simply and easily by incorporating it into a well-known *Escherichia coli* vector system in order to transform it. Also, no case is known where a selective and high level reaction is performed targeting nitrile compounds, in particular, aromatic polynitrile compounds, by a recombinant using such a nitrilase gene.

The nitrile compound used as a starting material in the present invention is an aliphatic or aromatic compound having one nitrile group, or an aliphatic or aromatic polynitrile compound having a plurality of nitrile groups. When the starting material used is orthophthalonitrile, isophthalonitrile or terephthalonitrile, the corresponding o-, m-, or p-cyanobenzoic acid can be preferably obtained in high purity.

In the present invention, the conversion reaction may be performed by adding a starting material substance and cells, cell-free extract or enzyme having the conversion activity, to a dilute aqueous solution, such as a phosphate buffer solution, at a pH of from 5 to 10, preferably from 6 to 8, and a temperature of from 15 to 45° C., preferably from 30 to 42° C.

The method for collecting the product produced in the reaction solution is not particularly limited but, for example, the supernatant of the reaction solution is separated and recovered, and thereafter the product may be obtained using a method such as precipitation formation, extraction, distillation, or combinations thereof, according to the properties of the product. Also, the product can be obtained in high purity by performing separation and purification using column chromatography or the like.

3. Nitrile Hydratase Gene and Amidase Gene Derived from *Rhodococcus* Bacteria

The chromosomal DNA, for example, of the *Rhodococcus* sp. ATCC39484 strain can be prepared by applying the method of Saito et al. (see, *Biochem. Biophys. Acta.,* 72, 619(1963)). The chromosomal DNA library for use in the cloning of the gene can be manufactured using, for example, a plasmid vector pUC18. The cloning of the nitrile hydratase gene and amidase gene can be performed by colony hybridization using a partial fragment prepared, for example, by the polymerase chain reaction (PCR) method by Saiki et al. (see, *Science* 230, 1350 (1985)) as a probe. At this time, a universal primer (forward or reverse) is used as one primer in PCR and for another primer, an appropriate sequence is selected from the DNA sequence coding for an object enzyme protein N terminal sequence being analyzed. By combining these primers, an anchor PCR is performed using the chromosomal DNA library as a template and thereby the coding sequence fragment of the objective enzyme can be obtained. By using the nitrile hydratase gene encoding sequence DNA fragment or amidase encoding sequence DNA fragment as a probe for the screening of all gene regions, a recombinant DNA containing a nitrile hydratase gene and/or amidase gene can be obtained from the chromosomal DNA library of the *Rhodococcus* sp. ATCC39484 strain. The DNA sequences of the nitrile hydratase encoding sequence fragment and amidase encoding sequence fragment can be determined using known method such as dideoxy method described by Sanger et al. (see, *Proc. Natl. Acad. Sci. USA.*, 74, 5463 (1997)).

In order to produce an enzyme using the thus-obtained enzyme structural gene, the enzyme structural gene is ligated with an appropriate expression vector, for example, downstream from the lac promoter of pUC8. Using the thus-obtained plasmid, a host such as *Escherichia coli* JM101 is transformed. By culturing the obtained transformants, the objective nitrile hydratase and/or amidase are or is produced in a very large amount within the host cells. The enzyme or enzymes may be used in the form of intact cells for the conversion reaction but a cell-free extract or purified enzyme obtained from the extract may also be used.

In order for enzyme genes derived from different microorganisms to be expressed in a host microorganism in a manner such that it actually functions therein, it is well known that various requirements must be satisfied, for example, that the gene is actually retained and divided in the host microorganism, that the gene is transcribed by the transcription function of the host, that the transcribed information is translated into a protein, that the polypeptide produced by the translation is folded into a higher dimensional structure so that it can have a function, that an enzyme is secreted in the same manner as in the donor microorganism so that the enzyme can contact a substrate, or if the enzyme is an intracellular enzyme, the host microorganism has a permeation/transportation system similar to those of the donor microorganism, and so on. Further, in order for the expression to be in some degree useful for industrial application, each of the requirements must be satisfied at high levels. To solve these problems, usually, operations such as analysis and modification of regulating regions, e.g., promoters, adaptation of transcription/expression system and various cofactors to the body of the target gene by constructing a complicated shuttle vector and returning cloned gene to the donor microorganism and the like become necessary. These methods have the problems in that it is difficult to obtain information on the target of analysis and to modify method of modification for the regulating mechanism, which must rely on a trial and error method, and that they are limited by the ability of the donor in performing the expression by returning the cloned gene to the donor. As far as the present inventors are aware, although some cases exist where nitrile hydratase gene and amidase gene of different microorganisms have been obtained and some cases where the expression of such nitrile hydratase and amidase has been confirmed, no case is known where a nitrile hydratase gene and amidase gene are obtained which catalyze selective hydrolysis of polynitrile and which can exhibit high activity highly exceeding the ability of the donor microorganism simply and easily by incorporating them into a well-known *Escherichia coli* vector system to transform it. Also, no case is known where selective and high level reaction is performed targeting nitrile compounds, in particular, aromatic polynitrile compounds by a recombinant using such nitrile hydratase gene and amidase gene.

The process for producing the carboxylic acids or amides conversion reaction of the present invention may be performed by adding a starting material substance and cells, cell-free extract or enzyme having the conversion activity, to a dilute an aqueous solution such as a phosphate buffer solution, at a pH of from 5 to 10, preferably from 6 to 8, and a temperature of from 15 to 45° C., preferably from 30 to 42° C. The product produced in the reaction solution may be obtained using a precipitation formation or column chromatography, depending on the property of the product.

The nitrile used as a starting material in the present invention is an aliphatic or aromatic compound having at least one nitrile group in the molecule. Preferred examples thereof include aromatic polynitrile compounds such ortho-phthalonitrile, isophthalonitrile, and terephthalonitrile.

The amide used as a starting material of the process for producing carboxylic acids according to the present invention is an aliphatic or aromatic compound having an amide group. Preferred examples thereof include aromatic amide compounds having a cyano group such as o-, m-, or p-cyanobenzamide.

Hereinafter, the present invention will be described more specifically by examples. However, the present invention should not be construed as being limited thereto.

EXAMPLE 1

Acquisition of Variant Microorganism

*Rhodococcus* sp. ATCC39484 (obtained from American Type Culture Collection in U.S.A.) was streaked in an LB agar culture medium and cultured for 24 hours in a constant temperature bath at 30° C. From the colonies generated, one loopful of cells was picked up and inoculated in 5 ml of LB liquid medium and cultured under shaking in a shaker at 30° C. for 6 hours. The cells were recovered by the centrifugation of 10,000 g, washed three times with isovolume 50 mM potassium/sodium phosphate buffer solution (pH: 7.0), and again suspended in the same isovolume buffer solution.

To the cell suspension, 2,000 ppm of NTG (N-methyl-N'-nitro-N-nitrosoguanidine) solution was added to have a final concentration of 100 ppm. After thoroughly stirring, the solution was left standing at room temperature for 30 minutes. Then, the cells were recovered by the centrifugation of 10,000 g, washed once with the same buffer solution and again suspended in a slight amount of the same buffer solution. Thereafter, the entire amount of the cells were inoculated in 5 ml of an inorganic salt liquid medium containing 0.1% of benzamide. The composition of the inorganic salt medium is shown below.

| (Inorganic Salt Culture Medium) | |
|---|---|
| $KH_2PO_4$ | 1.5 g/l |
| $Na_2HPO_4$ | 1.5 g/l |
| $MgSO_4$ 7 aq. | 0.2 g/l |
| $CaSO_4$ 2 aq. | 10 mg/l |
| $FeSO_4$ 7 aq. | 5 mg/l |
| Yeast extract | 20 mg/l |

After the shaking culture at 30° C. for 15 hours, ampicillin was added so as to have a concentration of 1 mg/L, and further cultured under shaking at 30° C. for 12 hours. The culture solution obtained was 500-fold diluted and the dilution solution was spread on 300 plates of LB solid media (each on a Petri dish having a diameter of 90 mm) in an amount of 0.1 ml per plate. Then the cells were cultured at 30° C. for 48 hours and when colonies were generated, the colonies were copied to an autoclaved velvet, each Petri dish as a whole was transcribed to an inorganic salt solid medium (diameter: 90 mm) having the above-described composition and containing 0.1% of benzamide and 1.5% of agar, and the cells were cultured at 30° C. for 48 hours.

The colony formation was compared between the solid medium as a transcription original and the inorganic salt solid medium as a transcription target, and about 400 strains which grew well in the LB and not in the inorganic salt solid medium were selected. These selected strains were transplanted from the transcription original LB to a new LB solid medium by means of sterilized toothpick and cultured at 30° C. for 24 hours. All colonies generated were inoculated in 5 ml of the above-described inorganic salt culture medium and 0.1% isophthalonitrile was added thereto and reacted at 30° C. for 48 hours. The parent strain ATCC39484 was also cultured, inoculated, and reacted in the same manner. The supernatant of the reaction solution obtained with each strain was diluted 100-fold and subjected to reverse phase HPLC (column: Shodex DS-613, eluant: 50% acetonitrile/5 mM potassium phosphate buffer solution, pH: 3.0, flow rate: 1 mL/min, detection: UV 210 nm). In one strain (SD826 strain), it was verified that a large amount of 3-cyano benzoic acid was detected similarly to the parent strain ATCC39484 and 3-cyanobenzamide and phthalic acid monoamide, which were detected in the reaction solution of the parent strain, were extremely reduced. The strain obtained was considered to be an objective strain defective in the side reaction route.

Table 1 below describes the mycological properties of novel *Rhodococcus* bacterium, *Rhodococcus* sp. SD826 (FERM BP-3705).

TABLE 1

Mycological Properties of *Rhodococcus* sp. SD826

| Item | Property |
|---|---|
| Morphology | Polymorphic rod |
| Gram stain | + |
| Spore | − |
| Motility | − |
| Behavior to oxygen | Aerobic |
| Oxidase | − |
| Catalase | + |
| Acid fast | − |
| Color of colony | Orange |
| Rod-coccus cycle | + |
| Adenine decomposition | + |
| Tyrosine decomposition | + |
| Urea decomposition | − |
| Assimilability | |
| Inositol | − |
| Maltose | − |
| Mannitol | + |
| Rhamnose | − |
| Sorbitol | + |
| p-Cresol | − |
| m-Hydroxybenzoic acid | + |
| Pimellic acid | + |
| Sodium adipate | + |
| Sodium benzoate | + |
| Sodium citrate | + |
| Sodium lactate | + |
| Testosteron | − |
| L-Tyrosine | + |
| Lactose | − |
| Mannose | + |
| 2,3-Butanediol | + |
| Glucose | + |
| Growth in the presence of 0.02% sodium azide | − |
| Growth at 10° C. | − |
| Growth at 40° C. | + |
| Growth at 45° C. | − |

EXAMPLE 2

*Rhodococcus* sp. SD826 was streaked in an LB agar culture medium and cultured in a constant temperature bath at 30° C. for 24 hours. From the colonies generated, one loopful of cells were picked up and suspended in 100 mL of an LB liquid medium placed in a 500 mL-volume baffled flask. The flask was placed in a constant temperature rotary shaker at 30° C. and cultured with 120 revolutions per minute for 24 hours. The microorganism cells obtained were recovered by the centrifugation of 10,000 g and suspended in a 50 mM sodium/potassium phosphate buffer solution (pH: 7) isovolume to the culture solution. To the cell suspension, isophthalonitrile corresponding to 5% (mass/volume) was added, the suspension was placed in a constant temperature rotary shaker at 30° C., and the reaction was performed with 120 revolutions per minute for 72 hours.

The reaction solution obtained was adjusted to a pH of 2 using 2 mol/l of hydrochloric acid, ethyl acetate isovolume to the reaction solution was added, and the resulting solution was stirred and extracted. The ethyl acetate layer obtained was appropriately diluted and analyzed by reverse phase HPLC (column: Shodex DS-613: eluant: 50% acetonitrile/5 mM potassium phosphate buffer solution, pH: 3.0, flow rate: 1 mL/min, detection: UV 210 nm). In the reaction solution, the main ingredients having a peak whose retention time was coincident with the 3-cyanobenzoic acid sample was found. The peak ingredients were collected and subjected to GC-mass spectral analysis. As a result, each was verified to delineate a fragment pattern suggesting the same structure as the sample.

As a comparative example, the reaction, extraction, and analysis were performed in the same manner as above except for using a parent strain ATCC39484. The main ingredients in the reaction solution of the parent strain were subjected to LC-MS analysis and identified.

The comparison between the reaction solution of the parent strain and the reaction solution of SD826 with respect to the concentration of each main component and estimated conversion ratio from isophthalonitrile which was a reaction starting material, and the reduction ratio of by-products owing to the use of SD826 strain based on ATCC39484 are shown in Table 2 below.

TABLE 2

| Name of Strain | m-Cyanobenzoic acid Concentration (%) | m-Cyanobenzoic acid Conversion (mol %) | m-Cyano-benzamide Concentration (%) | m-Cyano-benzamide Conversion (mol %) | Isophthalic acid monoamide Concentration (%) | Isophthalic acid monoamide Conversion (mol %) |
|---|---|---|---|---|---|---|
| ATCC39484 | 5.638 | 98.22 | 0.023 | 0.40 | 0.087 | 1.34 |
| SD826 | 5.721 | 99.67 | 0.003 | 0.06 | 0.016 | 0.24 |
| Reduction ratio in by-products/component (%) | | | 85 | | 82 | |
| Reduction ratio in by-products/total (%) | | | | 83 | | |

TABLE 3

| Name of Strain | p-Cyanobenzoic acid Concentration (%) | p-Cyanobenzoic acid Conversion (mol %) | p-Cyano-benzamide Concentration (%) | p-Cyano-benzamide Conversion (mol %) | Terephthalic acid monoamide Concentration (%) | Terephthalic acid monoamide Conversion (mol %) |
|---|---|---|---|---|---|---|
| ATCC39484 | 1.129 | 98.31 | 0.006 | 0.53 | 0.012 | 0.97 |
| SD826 | 1.145 | 99.68 | n.d. | — | 0.002 | 0.26 |
| Reduction ratio in by-products/component (%) | | | 100 | | 83 | |
| Reduction ratio in by-products/total (%) | | | | 89 | | | n.d.: Not detected

EXAMPLE 3

*Rhodococcus* sp. SD826 was streaked in an LB agar culture medium and cultured in a constant temperature bath at 30° C. for 24 hours. From the colonies generated, one loopful of cells were picked up and suspended in 100 ml of an LB liquid medium in a 500 mL-volume baffled flask. The flask was placed in a constant temperature rotary shaker at 30° C. and cultured with 120 revolutions per minute for 24 hours. The microorganism cells obtained were recovered by the centrifugation of 10,000 g and then suspended in a 50 mM sodium/potassium phosphate buffer solution (pH: 7) isovolume to the culture solution.

To the cell suspension, isophthalonitrile in an amount corresponding to 1% (mass/volume) and 0.1% (mass/volume) of benzonitrile as an inductive substrate were added. Then, the suspension was placed in a constant temperature rotary shaker at 30° C. and the reaction was performed with 120 revolutions per minute for 72 hours. The resulting reaction solution was adjusted to a pH of 2 using 2 mol/l of hydrochloric acid, added to ethyl acetate isovolume to the reaction solution, stirred, and then extracted. The ethyl acetate layer obtained was appropriately diluted and analyzed by reverse phase HPLC (column: Shodex DS-613, eluant: 50% acetonitrile/5 mM potassium phosphate buffer solution, pH: 3.0, flow rate: 1 mL/min, detection: UV 240 nm). In the reaction solution, main ingredients having a peak of which retention time was coincident with the 4-cyanobenzoic acid sample were found. The peak ingredients were collected and subjected to GC-mass spectral analysis and as a result, each was verified to delineate a fragment pattern suggesting the same structure as the sample.

As a comparative example, the reaction, extraction, and analysis were performed in the same manner as above except for using a parent strain ATCC39484. The main product in the reaction solution of the parent strain under the above-described HPLC conditions was subjected to LC-MS analysis and then identified and quantified.

The comparison between the reaction solution of the parent strain and the reaction solution of SD826 with respect to the concentration of each main ingredient and the estimated conversion ratio from isophthalonitrile, which was a reaction starting material, and the reduction ratio of by-products owing to the use of SD826 strain based on ATCC39484 are shown in Table 3 below.

EXAMPLE 4

Preparation of Chromosomal DNA for Preparing Nitrilase Gene

*Rodococcus* sp. ATCC39484 strain (hereinafter, referred to "R. sp.") was cultured a while day and night in an agar plate culture medium prepared by adding 2% of agar to an L broth (polypeptone: 1%, NaCl: 0.5%, yeast extract: 0.5%, pH: 7.0), and one loopful of cells thereof was cultured at 30° C. for 24 hours in 300 ml of a culture medium prepared by adding 5 g/l of glucose and 2 g/l of urea to a base culture medium ($KH_2PO_4$: 1.5 g/l, $NaHPO_4 2H_2O$: 0.75 g/l, $MgSO_4 7H_2O$: 0.2 g/l, $CaSO_4 2H_2O$: 10 mg/l, $FeSO_4 7H_2O$: 5 mg/l, yeast extract: 20 mg/l). The incubated cells were harvested and washed with 100 ml of 5 mM EDTA solution. The resulting cells were suspended in 30 ml of a buffer solution (20 mM Tris hydrochloric acid buffer solution (pH: 7.1)), 60 mg of lysozyme was added thereto, and the suspension was incubated at 37° C. for 2 hours. This suspension solution was centrifuged (5,000 rpm, 7 minutes) to recover the cells. The recovered cells were re-suspended in 11.34 mL of TE buffer, 0.6 ml of 10% SDS was added, proteinase R (produced by Merck) was added, and the mixture was gently shaken at 55° C. for 1 hour. This solution was extracted with phenol and precipitated with ethanol to prepare chromosomal DNA.

EXAMPLE 5

Construction of DNA Library

20 μg of the chromosomal DNA obtained in Example 4 was subjected to partial digestion using a restriction enzyme Sau 3AI. More specifically, the chromosomal DNA was charged into 5 tubes in an amount of 4 μg per tube and the restriction enzyme Sau 3AI (produced by Takara Shuzo Co., Ltd., from 4 to 12 U/μl) was added to each individual tube and reacted at 37° C. in a reaction volume of 100 μl. Every 10 seconds, one tube was taken up and the reaction was stopped by adding EDTA so as to have a final concentration of 20 mM. The thus-prepared partial digestion fragment solution of chromosomal DNA was electrophoresed with agarose gel, and from 1 to 2 kb of the DNA fragment was recovered through electrophoresis extraction and precipitation with ethanol. The DNA fragment recovered was then dissolved in 30 μl of TE solution. 9 μl of this sample and 1 μg of pUC18 (produced by Takara Shuzo Co., Ltd.) subjected to digestion with BamHI and to a BAP treatment were ligated using T4DNA ligase (ligation kit ver. 2, produced by Takara Shuzo Co., Ltd.) to make 20 µl and thereafter *Escherichia coli* JM101 strain was transformed. In order to prepare an amplified library from the library obtained, the *Escherichia coli* transformants were implanted by every 20 colonies on an L broth containing 50 ppm of ampicillin and cultured a whole day and night. From the cells, a plasmid was extracted by an alkali-SDS method.

EXAMPLE 6

Anchor pCR Method

In advance of cloning, anchor pCR was performed to obtain an enzyme gene partial fragment for use as a probe. One primer which was derived from the enzyme sequence was prepared by selecting a sequence having an appropriate Tm from known N-terminal sequences of this enzyme. That is, 5'-gct gcg gtg cag gca-3'

(and complementary strand thereof)

Tm: 52° C.

The PCR was performed under the following reaction conditions.

Composition of Reaction Solution:

| R. sp. ATCC39484 chromosomal DNA | |
|---|---|
| library | 1 µg |
| Universal primer | 100 pmol |
| Enzyme N-terminal primer | 100 pmol |
| dNTP Solution each | 1 mM |
| 10x Reaction buffer | 10 µl |
| EXTaqDNA Polymerase (produced by Takara Shuzo Co., Ltd.) | 2.5 U |
| | Total 50 µl |

Reaction Conditions:
 Denaturing: 94° C., 45 seconds
 Annealing: 37 to 55° C., 60 seconds
 Elongation: 72° C., 60 to 90 seconds
 Number of cycles: 24 times In the thus-performed reaction, a reaction solution found to have a fragment specifically amplified was subjected to 2% agarose gel electrophoresis and the region containing the fragment was cut off and purified using EASYTRAP ver. 2 (produced by Takara Shuzo Co., Ltd.). The DNA sequence of each of the DNA fragments obtained was determined by the dideoxy method. Those having a translated amino acid sequence homologous to the nitrilase N-terminal sequence of the R. sp. ATCC39484 strain were sought. As a result, an about 900 bp fragment containing the DNA sequence coding for nitrilase 287 amino acid was found in the fragments obtained.

EXAMPLE 7

Colony Hybridization

By using as a probe the PCR fragment obtained in Example 3 containing a part of the nitrilase gene, all genes were cloned by a colony hybridization method. The partial digestion fragment solution of chromosomal DNA degraded by Sau 3AI according to the method of Example 6 was subjected to 1% agarose gel electrophoresis, and a 4 to 8 kb DNA fragment was recovered through electrophoresis extraction and precipitation with ethanol. This fragment was dried and dissolved in 30 µl of TE solution. 9 µl of this sample solution and pUC18 (produced by Takara Shuzo Co., Ltd., 100 ng) subjected to digestion with 1 µg of BamHI and to a BAP treatment were ligated using T4DNA ligase (ligation kit ver. 2, produced by Takara Shuzo Co., Ltd.) and thereafter *Escherichia coli* JM101 strain was transformed. The transformants were spread on an agar plate culture medium prepared by adding 2% of agar to an L broth containing 0.1 mM of isopropyl-β-D-thiogalactopyranoside (IPTG), 0.004% of 5-bromo-4-chloro-3-indolyl-β-D-galactopyranoside (X-gal) and 50 ppm of ampicillin, and cultured at 37° C. a whole day and night.

The white colonies generated were picked up onto an agar plate culture medium prepared by adding 2% of agar to an L broth containing 50 ppm of ampicillin, and cultured at 37° C. a while day and night. After full growing, the agar plate culture medium was placed at 4° C. for about 2 hours to become chilled. A dry nylon membrane (Hybond-N+, produced by Amersham Pharmacia Biotech) was marked at the top, down, left, and right and then carefully placed on to a surface of the agar in contact with the colonies. After the membrane was entirely wetted, the membrane was removed from the agar surface in a single continuous movement to transfer the colonies on the plate to the membrane. When the number of cells transferred is small, the membrane was placed on an agar plate culture medium prepared by adding 2% of agar to L broth containing 50 ppm of ampicillin, and cultured at 37° C. a whole day and night.

The membrane having the cells transferred thereon was floated on 3 ml of an alkali solution (0.5M NaOH) to dissolve the cells. The undissolved residual cells were washed out from the membrane with 5×SSC for 20 minutes×2 times. To this membrane, colony hybridization was applied using Random prime DNA labeling and detection system (produced by Amersham Pharmacia Biotech). The detection by hybridization was performed under standard conditions according to the specification attached to the kit. As a result of hybridization performed on about 4,000 colonies, two strains were obtained as a positive clone.

From these positive clones, plasmids were extracted by an alkali-SDS method. The position of the cleavage site by the restriction enzyme in the partial fragment used as the probe was compared with the restriction digestion pattern of each plasmid, and therefrom the position and the direction of genes in the insertion fragment were estimated. As a result, the plasmids pNL06 and pNL09 prepared from two clone strains both were found to contain total nitrilase genes (see, FIG. 1). Using the P09 strain plasmid (pNL09) having a larger insertion fragment length, the DNA sequence of the insertion fragment of about 2.6 kb was determined. A portion homologous to the partial fragment sequence used as the probe was sought and as a result, it was found that a nitrilase gene was present in the positive direction with respect to the lac promoter from a portion about 300 bp downstream from the insertion fragment end. The thus-found direction and position agreed with the position and direction of the gene estimated from the cleavage site by the restriction enzyme. The amino acid sequence translated from this nitrilase gene sequence was novel and different from the amino acid sequence of any known nitrilase.

EXAMPLE 8

Measurement of Nitrilase Activity

The nitrilase activity was measured as follows. The cells were added to a reaction solution obtained by suspending from 1 to 10 mass % of terephthalonitrile (TPN) as a substrate in 10 ml of 20 mM phosphate buffer solution (pH: 7.0) and reacted at 30° C. while shaking, and the p-cyanobenzoic acid produced in the reaction solution was quantitated by HPLC at fixed intervals. The solid matter was removed from the reaction solution by centrifugation and the supernatant 100-fold diluted with the eluant was used as the HPLC sample. The apparatus and the conditions for the quantification of p-cyanobenzoic acid are shown below.

Apparatus:

| | |
|---|---|
| Pump: | DS-2 (Shodex) |
| Detector: | SPD-6AV UV-VIS spectrophotometer (Shimadzu) |
| Introduction of sample: | Autosampler Model 23 (SIC) with 20 ml sample tube |
| Recording: | Chromatocoder 12 (SIC) |
| Column: | ODSpak F-411 (Shodex), 4.6 × 150 mm, 40° C. |

Separation conditions:
AcCN/$H_2O$=50:50, 0.1% TFA, 1 ml/min.

The activity was shown by the mass of p-cyanobenzoic acid when cells in a dry mass of 1 g were produced in 1 l of the reaction solution within 1 hour (unit: g/l/hr/g dry cells).

EXAMPLE 9

Preparation of High Expression Strain

The positive clone P09 strain obtained in Example 4 was cultured in an L broth containing 50 ppm of ampicillin and as a result, nitrilase activity was confirmed irrespective of the presence or absence of isopropyl-β-D-thiogalactopyranoside (IPTG). However, this activity was as low as a few tenths of the *Rhodococcus* microorganism that was a donor. In the P06 strain, the nitrilase activity was not observed at all.

In order to increase the production of the enzyme, two kinds of fragments, one containing only the enzyme structural gene portion and another containing the enzyme structural gene and the region of about 1.3 kb downstream therefrom were prepared by PCR. Using these, plasmids pUNLE1 and pUNLE2 each ligated immediately after the lac promoter of pUC18 were prepared. The primers and the reaction conditions used for the preparation of pCR fragments are shown below.

pUNLE1

(forward)

5'-aac atg gtc gaa tac aca aac-3'

(reverse)

5'-cc aag ctt tca gag ggt ggc tgt-3'

HindIII site pUNLE 2

(forward) the same as pUNLE1

(reverse) M13 primer M4

Composition of Reaction Solution:

| | |
|---|---|
| Plasmid DNA | 0.8 to 1 μg |
| Primers | each 100 pmol |
| dNTP Solutions | each 1 mM |
| 10x Reaction buffer | 10 μl |
| EXTaqDNA Polymerase (produced by Takara Shuzo Co., Ltd.) | 2.5 U |
| | Total 50 μl |

Reaction Conditions:

| | |
|---|---|
| Denaturing: | 94° C., 60 seconds |
| Annealing: | 55° C., 60 seconds |
| Elongation: | 72° C., 120 seconds |
| Number of cycles: | 24 times |

Figure 2:
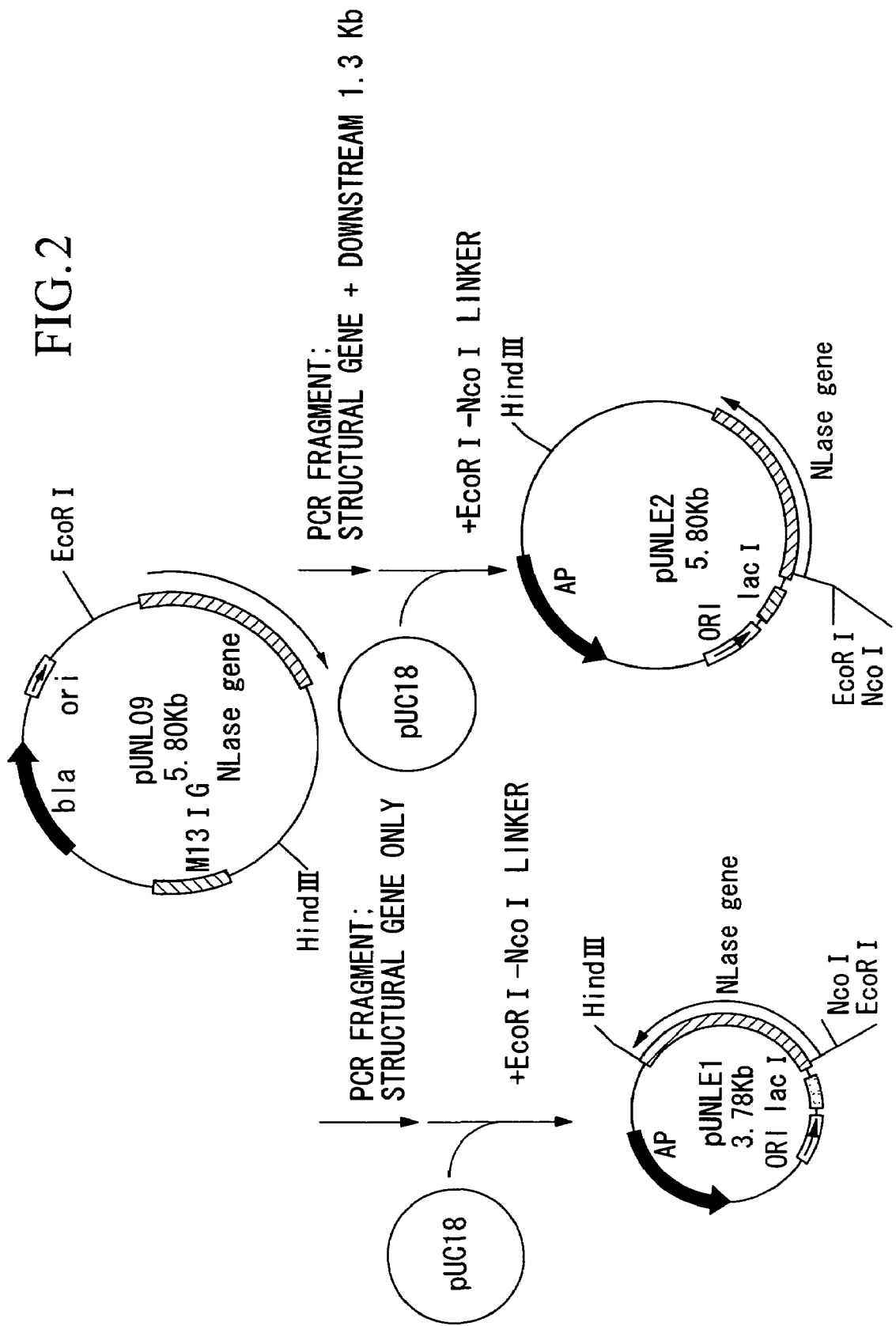
FIG. 2 is a schematic diagram illustrating the construction of a nitrilase gene expression plasmid.

The fragments produced were subjected to agarose gel electrophoresis and recovered by extraction. Each of the fragments was cut at the HindIII and NcoI site, ligated with EcoRINcoI linker, and then ligated with pUC18 cleaved at EcoRI and HindIII (see, FIG. 2). With these plasmids, *Escherichia coli* JM109 strain was transformed. The transformants obtained each was cultured in an L broth containing 50 ppm of ampicillin a whole day and night, and after adding isopropyl-β-D-thiogalacto-pyranoside (IPTG) to the culture solution to a concentration of 0.1 mM, was further cultured for 2 hours. The transformants obtained were measured on the nitrile conversion activity by the method described in Example 5. As a result, the transformants obtained by the transformation with any plasmid were verified to have a nitrilase activity as high as about 500 times the pUNL09 transformant and about 80 times the *Rhodococcus* microorganism which was a donor (see, Table 4)

TABLE 4

| Strain | Activity When Not Induced | Activity When Induced |
|---|---|---|
| R. sp. ATCC39484 | — | 0.14 |
| pUNL09 Transformant | 0.029 | 0.022 |
| pUNLE1 Transformant | 0.51 | 11.1 |
| pUNLE2 Transformant | 0.46 | 10.6 |

Activity unit: g/l/hr/g dry cells

EXAMPLE 10

Production of p-Cyanobenzoic Acid Using High Activity Strain

The pUNLE1 transformant obtained in Example 9 was cultured a whole day and night in an agar plate culture medium prepared by adding 2% of agar to an L broth containing 50 ppm of ampicillin, and the grown cells were inoculated with an inoculating loop in 100 ml of an L broth containing 100 ppm of ampicillin and cultured under shaking at 37° C. This culture solution was subcultured in a 5 L-volume jar fermenter filled with 2 l of L broth containing 100 ppm of ampicillin and cultured with aeration and stirring a whole day and night under conditions of 37° C., 800 rpm agitation, and an aeration rate of 1 l/min. To the cell culture solution at the initial stage of stationary phase or at the final stage of logarithmic growth phase, isopropyl-β-D-thiogalactopyranoside (IPTG) was added so as to have a final concentration of 0.1 mM, and the culturing was further continued for 4 hours.

Figure 3:
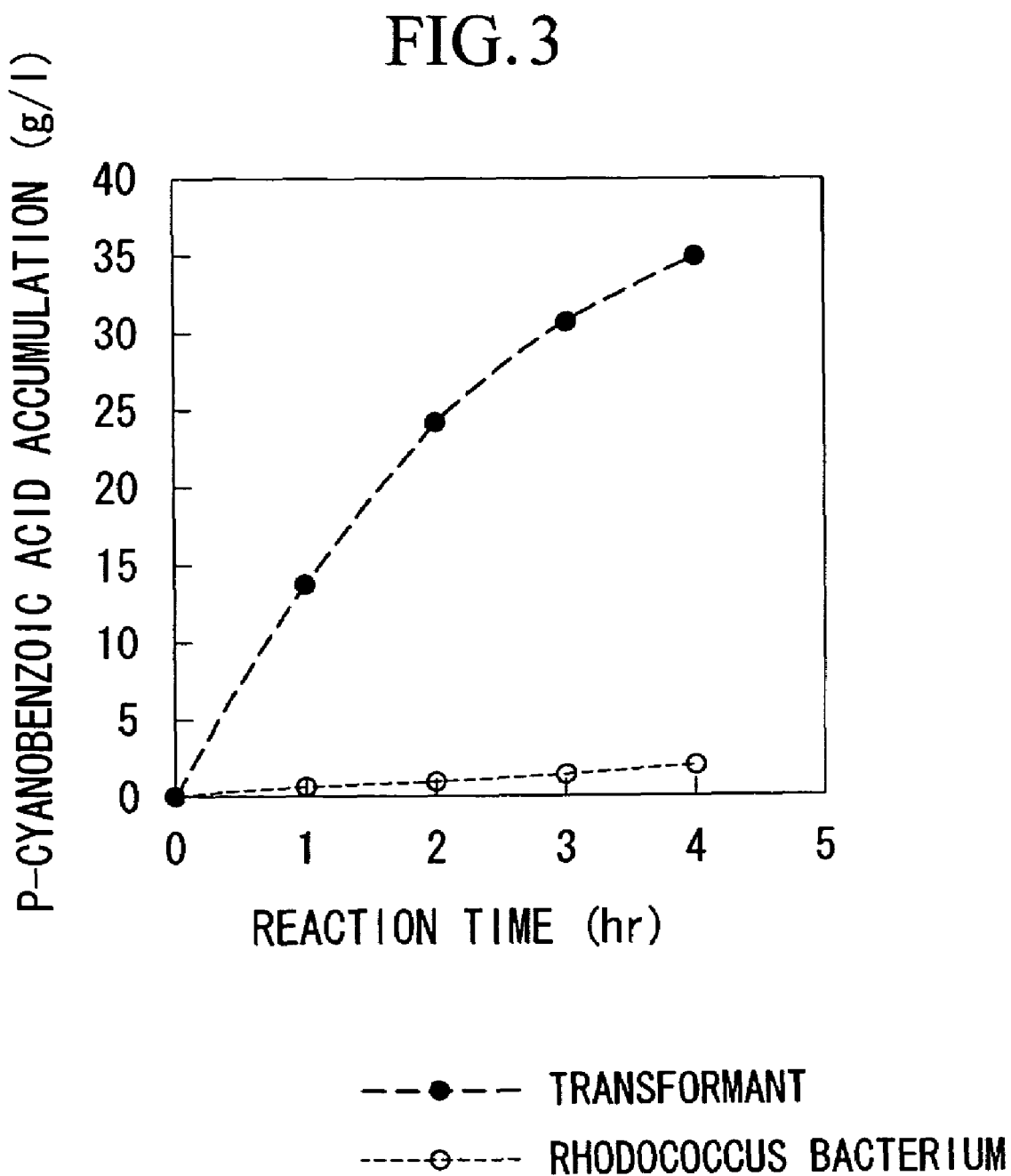
FIG. 3 is a graph showing a comparison of accumulation curves of p-cyanobenzoic acid in the conversion reaction from terephthalonitrile to p-cyanobenzoic acid.

The culture solution was centrifuged and the cells obtained were again suspended in 1 l of 20 mM phosphate buffer solution (pH: 7.0). Thereto, 100 g of terephthalonitrile (TPN) was added and reacted at 35° C. while stirring. A part of the reaction solution was sampled at intervals of one hour and the p-cyanobenzoic acid produced in the reaction solution was quantified by the method described in Example 5. The p-cyanobenzoic acid was quickly produced by the transformant and accumulated in a proportion of 3% in the reaction solution within about 3 hours (see, FIG. 3). After the completion of reaction, concentrated hydrochloric acid was added to the reaction solution to adjust the pH to 1 and thereby precipitate the p-cyanobenzoic acid. The precipitate was filtered through a filter paper, washed with dilute hydrochloric acid (0.1 mol/l), and then vacuum dried. The thus-obtained dry sample had a purity of 99.9% or more. The impurity detected was the starting material terephthalonitrile.

EXAMPLE 11

Preparation of Chromosomal DNA for Preparing Nitrile Hydratase Gene and Amidase Gene R. sp. ATCC 39484 strain was cultured a whole day and night in a nutrient (L broth) agar plate culture medium, and a loopful of cells thereof was cultured at 30° C. for 24 hours in 300 ml of a culture medium prepared by adding 5 g/l of glucose and 2 g/l of urea to a base culture medium ($KH_2PO_4$: 1.5 g/l, $Na_2HPO_4 2H_2O$: 0.75 g/l, $MgSO_4 7H_2O$: 0.2 g/l, $CaSO_4 2H_2O$: 10 mg/l, $FeSO_4 7H_2O$: 5 mg/l, yeast extract: 20 mg/l). The incubated cells were harvested and washed with 100 ml of 5 mM EDTA solution. The resulting cells were suspended in 30 ml of a buffer solution (20 mM Tris hydrochloric acid buffer solution (pH: 7.1)), 60 mg of lysozyme was added thereto, and the suspension was incubated at 37° C. for 2 hours. This suspension solution was centrifuged (5,000 rpm, 7 minutes) to recover the cells. The recovered cells were re-suspended in 11.34 mL of TE buffer, 0.6 ml of 10% SDS was added proteinase R (produced by Merck) was added to a concentration of 100 μg/ml, and the mixture was gently shaken at 55° C. for 1 hour. This solution was extracted with phenol and precipitated with ethanol to prepare chromosomal DNA.

EXAMPLE 12

Construction of a DNA Library

The 20 μg of the chromosomal DNA obtained was subjected to partial digestion using a restriction enzyme Sau 3AI. More specifically, the chromosomal DNA was charged into 5 tubes in an amount of 4 μg per tube, and the restriction enzyme Sau 3AI (produced by Takara Shuzo Co., Ltd., from 4 to 12 U/μl) was added to each individual tube and reacted at 37° C. in a reaction volume of 100 μl. Every 10 seconds, one tube was taken up and the reaction was stopped by adding EDTA to have a final concentration of 20 mM. The thus-prepared partially digested fragment solution of chromosomal DNA was electrophoresed with agarose gel, and from 5 to 10 kb of the DNA fragment was recovered through electrophoresis extraction and precipitation with ethanol. The recovered DNA fragment was then dissolved in 30 μl of TE solution. 9 μl of this sample and 1 μg of pUC18 (produced by Takara Shuzo Co., Ltd.) subjected to digestion with BamHI and BAP treatment were ligated using T4DNA ligase (ligation kit ver. 2, produced by Takara Shuzo Co., Ltd.) to yield 20 μl and thereafter *Escherichia coli* JM101 strain was transformed. In order to prepare an amplified library from the library obtained, the *Escherichia coli* transformants were implanted every 20 colonies on an L broth (pH 7.0) containing 50 ppm of ampicillin and cultured a whole day and night. From the cells, a plasmid was extracted by an alkali-SDS method.

EXAMPLE 13

Purification of Nitrile Hydratase and Amidase

One primer derived from the enzyme sequence necessary for anchor PCR was prepared from the N-terminal sequence of the enzyme peptide prepared as follows by selecting the sequence such that the primer has a suitable Tm.

The nitrile hydratase activity or amidase activity were each qualitatively determined by allowing 1 ml of a reaction mixture containing 10 mM benzonitrile or 10 mM benzamide, 30 mM potassium phosphate buffer (pH 7.0), and a predetermined amount of cell extract to react at 25° C. for 30 minutes and then detecting the produced benzamide or benzoic acid by HPLC (the HPLC separation conditions were the same as those in Example 8 described above).

R. sp. ATCC39484 strain was inoculated in 600 ml of a nitrile decomposition enzymes inducing medium consisting of the basic medium of Example 1 and 1 g/l of benzonitrile as an induction substrate, and cultured with shaking at 30° C. The culture solution cultured a whole day and night was subjected to centrifugation (8,000 rpm, 15 minutes) to recover the cells, and 3.2 g in wet weight of the obtained cells were washed with 50 ml of 100 mM potassium phosphate buffer (pH 7.0, containing 1 mM EDTA and 2 mM DTT), and thereafter, suspended in 200 ml of the same buffer. This was subjected super sonicator to destroy the cells, followed by centrifugation (12,000 rpm, 20 minutes) to obtain 180 ml of a supernatant (crude enzyme extract solution).

Ammonium sulfate was added to this cell-free extract solution to a 45% saturation concentration, the mixture was stirred at 4° C. for 1 hour, and then the generated precipitates were removed by centrifugation. Further, ammonium sulfate was added to the separated supernatant to a 60% saturation concentration, the mixture was stirred at 4° C. for 1 hour, and thereafter the precipitates were recovered by centrifugation. The generated precipitates were confirmed to exhibit nitrile hydratase activity and amidase activity. The obtained precipitates were dissolved in 10 ml of a 100 mM potassium phosphate buffer (pH 7.0, containing 1 mM EDTA and 2 mM DTT), and the solution was dialyzed against the same buffer.

The dialyzed crude enzyme solution was charged in a DEAE-Sepharose column (2 cm×20 cm) equilibrated with a 100 mM potassium phosphate buffer (pH 7.0, containing 1 mM EDTA and 2 mM DTT) and washed with the equilibrated buffer until the UV absorption at 280 nm of the eluate decreased. Subsequently, it was further washed with the same buffer but supplemented with 0.1 M KCl until the UV absorption at 280 nm of the eluate decreased. Thereafter, nitrile hydratase and amidase were eluted with a 100 mM potassium phosphate buffer (pH 7.0, containing 1 mM EDTA and 2 mM DTT) with KCl concentration being increased to 0.3 M. Fractions showing the activity were collected and the enzyme protein was concentrated using an ultrafiltration membrane (molecular weight 30,000 cut).

In Phenyl Sepharose CL-4B column (2 cm×40 cm) equilibrated with a 100 mM potassium phosphate buffer (pH 7.0, containing 10% saturation concentration of ammonium sulfate), and a mixture of the concentrated active fraction and 10% saturation concentration of ammonium sulfate was charged to allow the enzyme to be adsorbed thereon. Then, the column was washed with the equilibration buffer until the UV absorption at 280 nm of the eluate decreased. Thereafter, nitrile hydratase and amidase were eluted with the elution buffer (100 mM potassium phosphate buffer (pH 7.0)). The active fractions were collected and the enzyme protein was concentrated using ultrafiltration membrane (molecular weight 30,000 cut).

The concentrated nitrile hydratase active fraction was charged in a Sepharcryl S-300 Superfine Column (2 cm×60 cm), equilibrated with a 100 mM potassium phosphate buffer (pH 7.0, containing 0.5 M NaCl), and separation was performed using the same buffer, thus fractionating the eluate into about 0.5 ml fractions. In this stage, different fractions indicated the maximal nitrile hydratase and amidase activities, respectively so that the fraction showing the highest enzyme activity and the neighboring fractions were recovered for each enzyme. About 1.5 ml each of fraction was concentrated using an ultrafiltration membrane (molecular weight 30,000 cut).

EXAMPLE 14

Determination of Peptide Terminal Sequence

Determination of the N-terminal sequences of the obtained nitrile hydratase and amidase was tried, but both enzymes showed low signal intensity in Edman decomposition so that the determination of sequences was unsuccessful. Accordingly, the enzyme protein was hydrolyzed by a cyanogen bromide (BrCN) and the produced peptides were separated under the following liquid chromatography conditions.

| Body; | LC 9A (Shimadzu Seisakusho) |
|---|---|
| Column; | Asahipak ODP 50 6D (Shodex) |
| Column temperature; | 25° C. |
| Eluant; | Acetonitrile 0 to 80% (linear Concentration gradient, 60 minutes) 0.1% Trifluoroacetic acid Flow rate: 0.5 ml/min. |
| Detection; | SPD-6AV UV VIS Spectro Photometer (Shimadzu Seisakusho) 215 nm |

Of the plurality of peptides obtained from the nitrile hydratase active fractions, those samples which showed relatively good separation were selected and subjected again to N-terminal sequence analysis by Edman decomposition. As a result, the following sequence having a high homology with the existing nitrile hydratase sequence was confirmed.

Glu(E) • Tyr(Y) • Arg(R) • Ser(S) • Arg(R) • Val(V) • Val(V)

Taking into consideration this sequence and the codon usage of *Rhodococcus* bacteria, a primer for nitrile hydratase was prepared.

5'-GAG TAC CGG TCC CGA-3' (and complementary strand thereof)

Similarly, of the plurality of peptides obtained from the amidase active fractions, those fractions showing relatively good separation were selected and subjected again to N-terminal sequence analysis by Edman decomposition. As a result, the following sequence having a high homology with the existing amidase sequence was confirmed.

Ala(A) • Val(V) • Gly(G) • Gly(G) • Asp(D) • Gln(O) • Gly(G)

Taking into consideration this sequence and the codon usage of *Rhodococcus* bacteria, a primer for amidase was prepared.

5'-GCA GTC GGC GGC GAC-3' (and complementary strand thereof)

EXAMPLE 15

Anchor PCR Method

The PCR method was performed under the following reaction conditions:

Composition of Reaction Solution:

| R sp. ATCC39484 chromosomal DNA | |
|---|---|
| library | 1 μg |
| Universal primer | 100 pmol |
| Enzyme peptide N-terminal primer | 100 pmol |
| dNTP Solution | each 1 mM |
| 10x Reaction buffer | 10 μl |
| EXTaqDNA Polymerase (produced by Takara Shuzo Co., Ltd.) | 2.5 U |
| | Total 50 μl |

Reaction Conditions:
  Denaturing: 94° C., 45 seconds
  Annealing: 37 to 60° C., 60 seconds
  Elongation: 72° C., 60 to 90 seconds
  Number of cycles: 24 times In the thus-performed reaction, a reaction solution found to have a fragment specifically amplified was subjected to 2% agarose gel electrophoresis and the region containing the fragment was cut off and purified using EASYTRAP ver. 2 (produced by Takara Shuzo Co., Ltd.). Each of the DNA fragments obtained was determined on the DNA sequence by the dideoxy method to confirm that the translated amino acid sequence have homology to the known nitrile hydratase or amidase. As a result, it was revealed that obtained fragments 4 and 14 contained sequences having a high homology with the known nitrile hydratase and amidase, respectively. Fragment 4 contained an about 500 bp a nitrile hydratase homologous sequence and fragment 14 contained an about 900 pb amidase homologous sequence. Both had sufficient lengths for serving as a probe for use in the subsequent colony hybridization.

EXAMPLE 16

Colony Hybridization

By using as a probe the PCR fragments containing a part of the nitrile hydratase gene and the PCR fragments containing a part of amidase gene, obtained in Example 15, full genes were cloned by a colony hybridization method. The partial digestion fragment solution of chromosomal DNA degraded by Sau 3AI according to the method of Example 1 was subjected to 1% agarose gel electrophoresis, and a 4 to 8 kb DNA fragment was recovered through electrophoresis extraction and precipitation with ethanol. This fragment was dried and dissolved in 30 µl of TE solution. 9 µl of this sample solution and 1 µl of pUC18 (produced by Takara Shuzo Co., Ltd., 100 ng) subjected to digestion with BamHI and BAP treatment were ligated using T4DNA ligase (ligation kit ver. 2, produced by Takara Shuzo Co., Ltd.), and thereafter *Escherichia coli* JM101 strain was transformed. The transformants were spread on an agar plate culture medium prepared by adding 2% of agar to an L broth containing 0.1 mM of isopropyl-β-D-thiogalactopyranoside (IPTG), 0.004% of 5-bromo-4-chloro-3-indolyl-β-D-galactopyranoside (X-gal) and 50 ppm of ampicillin, and cultured at 37° C. a whole day and night.

The white colonies generated were picked up onto an agar plate culture medium prepared by adding 2% of agar to an L broth containing 50 ppm of ampicillin, and cultured at 37° C. a whole day and night. After full growing, the agar plate culture medium was placed at 4° C. for about 2 hours so as to be chilled.

A dry nylon membrane (Hybond-N+, produced by Amersham Pharmacia Biotech) was marked with a pencil at the top, down, left and right, and then carefully placed on to a surface of the agar in contact with the colonies. After the membrane was entirely wetted, the membrane was gently removed from the agar surface, and in a single continuous movement the colonies on the plate were transferred to the membrane. When the number of cells transferred is small, the membrane was placed on an agar plate culture medium prepared by adding 2% of agar to L broth containing 50 ppm of ampicillin, and cultured at 37° C. a whole day and night.

The membrane having transferred thereon the cells was floated on 3 ml of an alkaline solution (0.5M NaOH) to dissolve the cells. The undissolved residual cells were washed out from the membrane with 5×SSC for 20 minutes×2 times. To this membrane, colony hybridization was applied using Random prime DNA labeling and detection system (produced by Amersham Pharmacia Biotech). The detection by hybridization was performed under standard conditions according to the specifications attached to the kit. As a result of hybridization performed on about 8,000 colonies, one strain for each gene was obtained as a positive clone.

Figure 4:
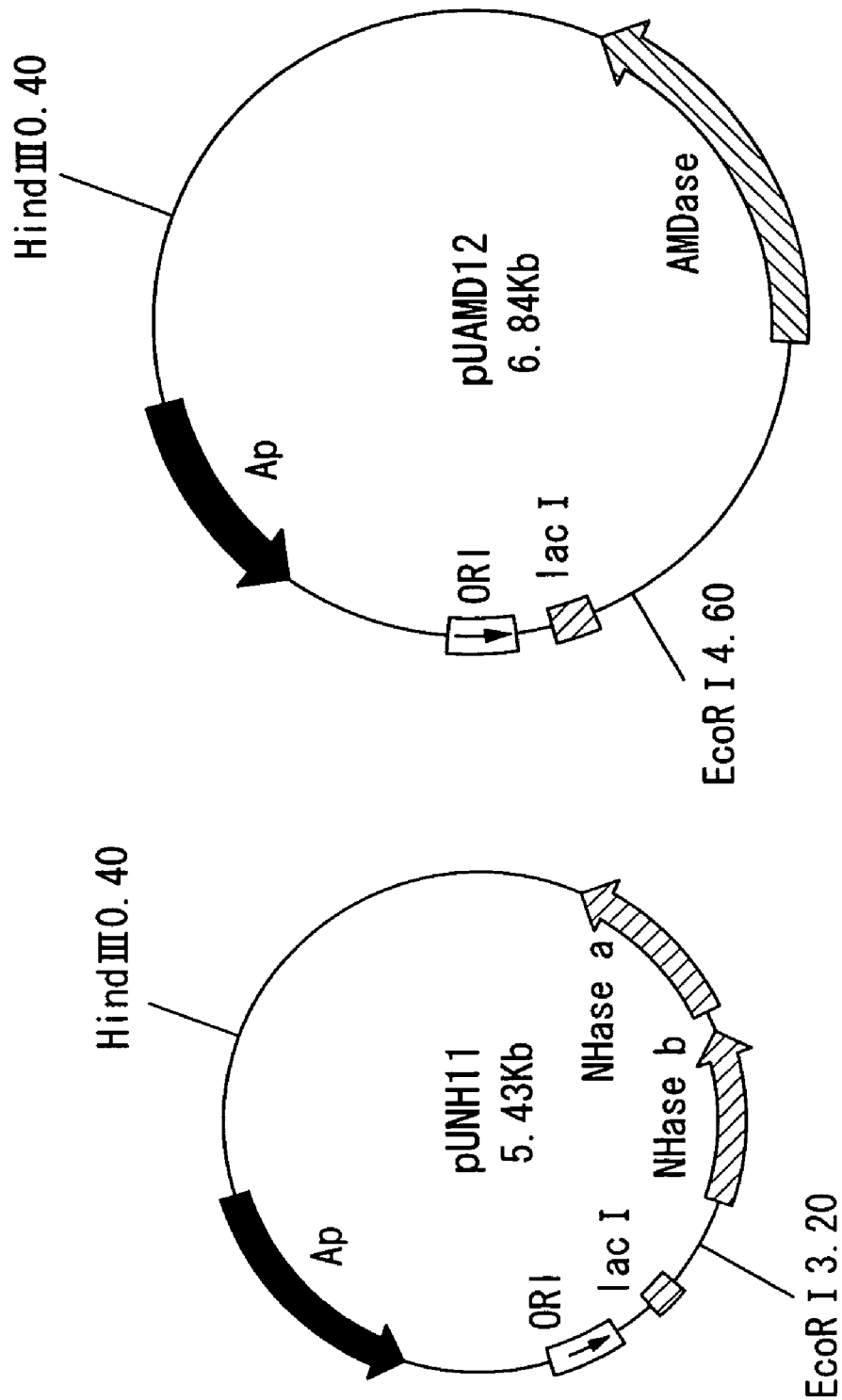
FIG. 4 is a schematic diagram illustrating the structure of a plasmid prepared from a cloned strain.

From these positive clones, plasmids were extracted by an alkali-SDS method. The position of the cleavage site by the restriction enzyme in the partial fragment used as the probe was compared with the restriction digestion pattern of each plasmid, and therefrom the position and the direction of genes in the insertion fragment were estimated. As a result, the plasmid UNH11 prepared from cloned strain P11 of nitrile hydratase was revealed to contain the whole nitrile hydratase gene (see, FIG. 4), while the plasmid pUAMD12 prepared from the cloned strain P12 of amidase showed complex restriction enzyme treatment pattern and the position and direction of the gene could not be determined. Accordingly, pUAMD12 alone was further treated with restriction enzyme and the obtained fragments were subjected to Southern hybridization. From the results, it was presumed that this also contained the whole structural gene regions (FIG. 4).

EXAMPLE 17

Preparation of Deletion Mutant and Determination of Base Sequence pUNH11 and pUAMD12 are plasmids each containing an inserted fragment of 3 kb to 4 kb, and their base sequence was difficult to determine. Thus, preparation of deletion mutants from which the inserted fragment was deleted from the terminal using exonuclease III was tried. For preparing the mutants, Deletion Kilo-Sequence Kit (Takara Shuzo Co., Ltd.) was used. That is, 25 µl (about 16 µg for 0.4 mg/ml) of pUNH11 or pUAMD 12 solution was fully digested with Sse8387I and XbaI (37° C., 24 hours), purified by extraction with phenol, and precipitated by addition of ¹/₁₀ volume of 3 M Na acetate and 2.5 volumes of ethanol. The precipitates were centrifuged and recovered and once washed with 70% cold ethanol. Thereafter, the precipitates were dried under vacuum. The vacuum dried precipitates were dissolved in 100 µl of Exo III buffer. 1 µl of Exonuclease III was added to the DNA solution and the mixture was stirred using a vortex, and thereafter incubated at 37° C. After 10 seconds and 30 seconds, each 50 µl of the reaction mixtures was sampled (mixed with 50 µl of a MB nuclease buffer prepared in advance to stop the reaction).

2 µl of MB nuclease was added to the reaction mixture and incubated at 37° C. for 20 minutes. After completion of the reaction, the reaction mixture was extracted with phenol for purification, and ¹/₁₀ volume of 3 M Na acetate and 2.5 volumes of ethanol were added to form precipitates. The precipitates were recovered by centrifugation, washed once with 70% cold ethanol, and then dried under vacuum. The thus-obtained precipitates were dissolved in 50 µl of Klenow buffer and 1 µl of Klenow fragment was added thereto, followed by incubation at 37° C. for 15 minutes. The reaction mixture was subjected to agarose gel electrophoresis to fractionate into three strand length ranges (each was cut out from the gel, extracted and recovered).

10 µl of recovery solution of the cut out fragment was mixed with 100 µl of ligation solution A, 12 µl of ligation solution B was added thereto, and the mixture was stirred at 16° C. for 24 hours using a vortex to cause self ligation. The obtained plasmid was used to transform the *Escherichia coli* JM109 strain.

By the above operation, 20 or more deletion mutants could be obtained for pUNH11. From these, 7 mutants containing insertion fragments with suitable lengths were selected and used for the determination of sequence. However, for pUAMD12, it was revealed that suitable deletion mutants could not be obtained because it generated plasmids greater than the original plasmid or plasmids smaller than the vector used. Accordingly, for pUAMD12, sequence determination by a gene walking method, which determines the sequence while the primer is sequentially synthesized, was performed.

The determination of a base sequence was performed according to a dideoxy method by using an about a 2.8 kb DNA sequence corresponding to the whole range of the inserted fragment for pUNH11, and an about 2.8 kb DNA sequence corresponding to about ⅔ of the inserted fragment for pUAMD12. Portions identical with partial fragment sequences used as a probe were searched and as a result it was revealed that about 0.2 kb and about 1.1 kb downstream from the insertion fragments of pUNH11 and pUAMD12 on the EcoRI site, the nitrile hydratase gene was present in a reverse direction to the lac promoter while the amidase gene was present in a forward direction thereto. The results of analysis of base sequences are shown by SEQ ID NO 3 and 6. The thus-found direction and position agreed with the position and direction of the gene estimated from the cleavage pattern by the restriction enzyme with respect to pUNH11, and agreed with the position and direction of the gene estimated from the cleavage pattern by the restriction enzyme, and the results of Southern hybridization with respect to pUAMD12. The amino acid sequences (SEQ ID NOs 4, 5 and 7) translated from these gene sequences were novel and different from the amino acid sequences of any known nitrile hydratase and amidase.

EXAMPLE 18

Measurement of Nitrile Hydratase and Amidase Activities

The nitrile hydratase activity was measured as follows. The cells (about 1 g by wet mass) were added to a reaction solution obtained by suspending from 1 to 10 mass % of terephthalonitrile (TPN) as a substrate in 10 ml of 20 mM phosphate buffer solution (pH: 7.0) and reacted at 30° C. while shaking, and the p-cyanobenzoic acid amide produced in the reaction solution was quantitated by HPLC at fixed intervals. The solid matter was removed from the reaction solution by centrifugation, and the supernatant 100-fold diluted with the eluant was used as the HPLC sample. The amidase activity was measured by using p-cyanobenzamide or benzamide serving as a substrate, performing the reaction under the same conditions as above, and determining the generated p-cyanobenzoic acid or benzoic acid by HPLC.

The products were determined using the apparatus and the conditions below:

Apparatus:

| Pump: | DS-2 (Shodex) |
|---|---|
| Detector: | SPD-6AV UV-VIS spectrophotometer (Shimadzu) |
| Introduction of sample: | Autosampler Model 23 (SIC) with 20 μl sample tube |
| Recording: | Chromatocoder 12 (SIC) |
| Column: | ODSpak F-411 (Shodex), 4.6 × 150 mm, 40° C. |

Separation conditions:

AcCN/$H_2O$=50:50, 0.1% TFA, 1 ml/min.

The activity was shown by the mass of p-cyanobenzoic acid amide, p-cyanobenzoic acid, or benzoic acid when cells in a dry mass of 1 g were produced in 1 l of the reaction solution within 1 hour (unit: g/l/hr/g dry cells).

EXAMPLE 19

Preparation of High Expression Strain

The positive clone P11 strain or P12 strain obtained in Example 16 was cultured in an L broth containing 50 ppm of ampicillin, and as a result, nitrile hydratase activity was confirmed irrespective of the presence or absence of isopropyl-β-D-thiogalactopyranoside (IPTG). However, this activity was as low as a few tenths of the *Rhodococcus* microorganism that was a donor. In the P12 strain, the amidase activity was not observed at all.

In order to increase the production of the enzyme, fragments of only the enzyme structural gene portions were prepared by PCR and ligated immediately after the lac promoter of pUC18 to prepare plasmids pUNHE1 and pUAMDE1. Further, plasmid pUNHAMDE1 having the both fragments on the same plasmid was prepared.

The primers and the reaction conditions used for the preparation of PCR fragments are shown below:

pUNLE1

(forward)

5'-acc atg gat ggt atc cac gac-3'

(β subuit initiation codon)(NcoI site)

(reverse)

5'-cc aag ctt tca tac gat cac ttc-3'

(α subuit stop codon)(HindIII site)

pUAMDE1

(forward)

5'-acc atg gct tcg ttg act cc-3'

(NcoI site, mutation of amino acid 3 Ser→Ala)

(reverse)

5'-cc aag ctt tca gga cgg cac cga-3'

(HindIII site)

Composition of Reaction Solution:

| Plasmid DNA | 0.8 to 1 μg |
|---|---|
| Primers | each 100 pmol |
| dNTP Solutions | each 1 mM |
| 10x Reaction buffer | 10 μl |
| EXTaqDNA Polymerase (produced By Takara Shuzo Co., Ltd.) | 2.5 U |
| | Total 50 μl |

Reaction Conditions:

| Denaturing: | 94° C., 60 seconds |
|---|---|
| Annealing: | 55° C., 60 seconds |
| Elongation: | 72° C., 120 seconds |
| Number of cycles: | 24 times |

Figure 5:
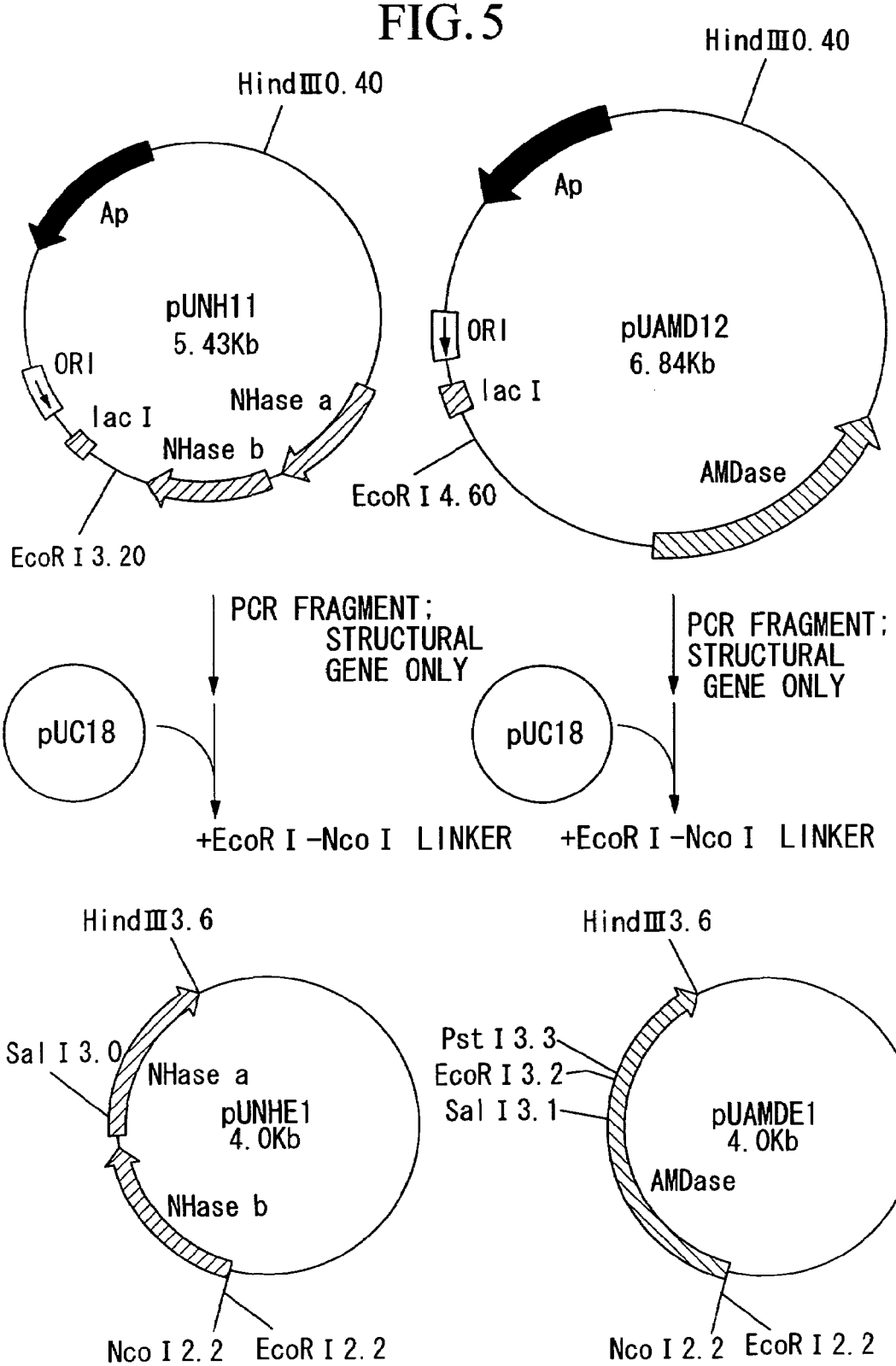
FIG. 5 is a schematic diagram illustrating the construction (1) of expression plasmid.

For both the nitrile hydratase gene and amidase gene, the fragments produced were subjected to agarose gel electrophoresis and recovered by extraction. The fragments each was cut at NcoI and HindIII sites, ligated with EcoRINcoI linker, and then ligated with pUC18 cleaved at EcoRI and HindIII (see, FIG. 5).

Figure 6:
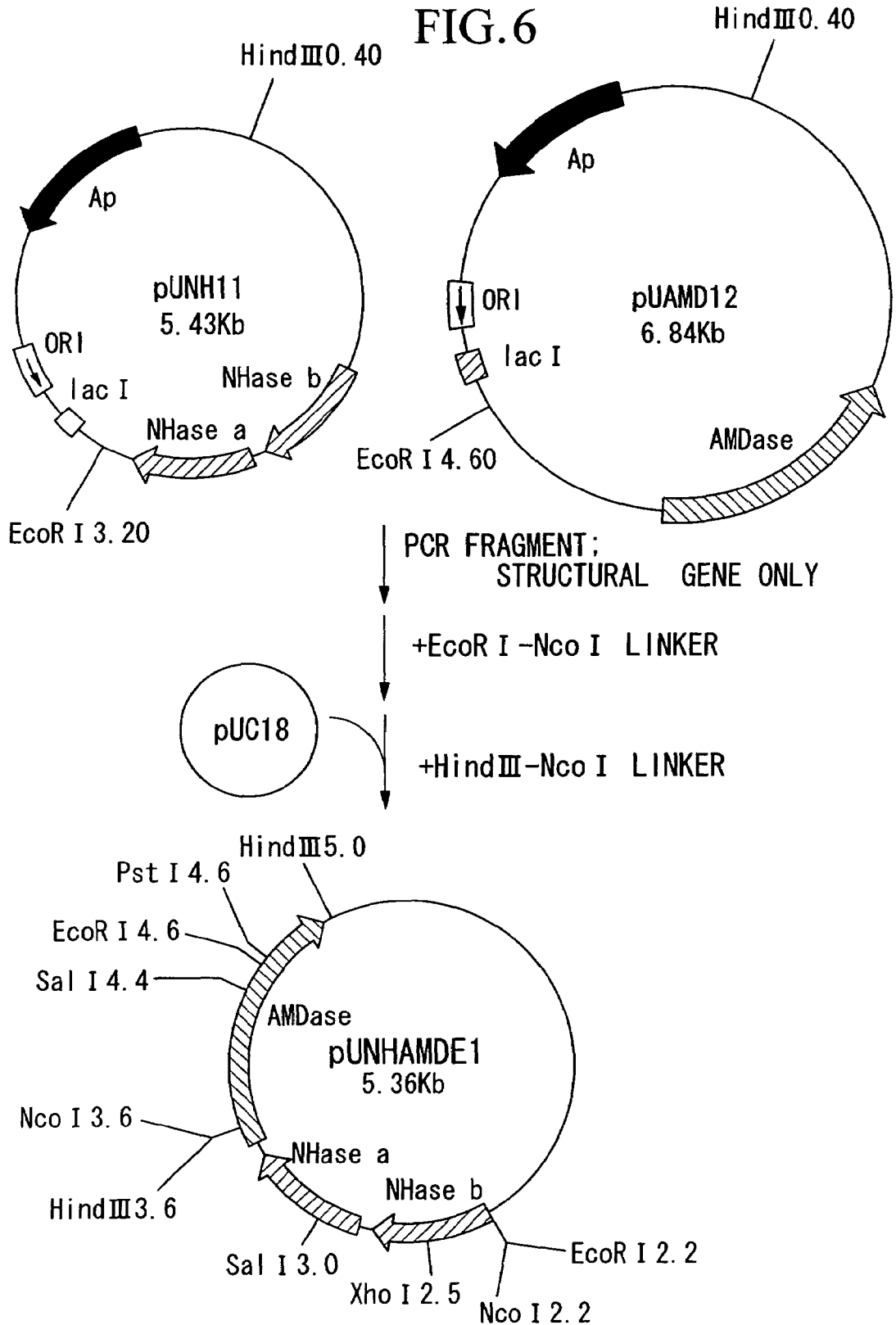
FIG. 6 is a schematic diagram illustrating the construction (2) of expression plasmid.

The plasmid on which the both the nitrile hydratase gene and the amidase gene are present was first digested with restriction enzymes NcoI and HindIII to cleave the nitrile hydratase fragment, the fragments were ligated with EcoRINcoI linker, HindIII-NcoI linker in order, thereafter ligated with the amidase fragment cleaved with NcoI and HindIII, and finally the resulting fragment was ligated with pUC18 cleaved with EcoIR-HindIII (FIG. 6).

With these plasmids, *Escherichia coli* JM109 strain was transformed. Each of the transformants obtained was cultured in an L broth containing 50 ppm of ampicillin over a twenty-four our period, and after adding isopropyl-β-D-thiogalactopyranoside (IPTG) to the culture solution to a concentration of 0.1 mM, further cultured for 2 hours. The transformants obtained were measured on the nitrile conversion activity by the method described in Example 8. As a result, the transformants obtained by the transformation with any plasmid were verified to have a nitrilase activity higher than that of the *Rhodococcus* bacterium, the donor. Only the transformant transformed with a plasmid having the both genes thereon showed activity as high as that of the donor. The results are summarized in Table 5 below.

TABLE 5

| Strain | Activity When Not Induced | Activity When Induced |
|---|---|---|
| R. sp. ATCC39484 | — | 0.17[1] |
| PUNH11 Transformant | 0.009 | 0.007 |
| PUAMD12 Transformant | n.d. | n.d. |
| PUNHE1 Transformant | 0.35 | 0.41 |
| PUAMDE1 Transformant | 0.11 | 0.27 |
| PUNHAMDE1 Transformant | 0.11[2] | 0.13[2] |

Activity unit: g/l/hr/g dry cells
[1] The activity of donor measured was amide generation rate only (acid generation rate was impossible to accurately measure due to the influence of nitrilase.)
[2] For pUNHAMDE1, the generation rate of acid from nitrile was measured.

Activity unit: g/l/hr/g dry cells

1) The activity of donor measured was amide generation rate only (acid generation rate was impossible to accurately measure due to the influence of nitrilase.)

2) For pUNHAMDE1, the generation rate of acid from nitrile was measured.

DESCRIPTION OF DEPOSIT

The following microorganism has been deposited at National Institute of Bioscience and Human-Technology, Agency of Industrial Science and Technology, Ministry of International Trade and Industry (1–3, Higashi 1-chome Tsukuba-shi Ibaraki-ken, Japan).

| Microorganism | Accession Number | Date of Deposition |
|---|---|---|
| Rhodococcus sp. SD826 | FERM BP-7305 | Oct. 12, 1999 |

The deposited microorganism has been deposited under the provisions of Budapest Treaty on International Recognition of the Deposit of Microorganisms for the Purposes of Patent Procedure and Rules based thereon.

---

The invention claimed is:

1. An isolated microorganism having an endogenous activity of converting a cyano group into a carboxyl group and being defective or reduced in an endogenous activity of a nitrile hydratase having the amino acid sequence of SEQ ID NO: 4 and/or SEQ ID NO: 5,
wherein said microorganism is a mutant strain of a microorganism belonging to the genus *Rhodococcus*.

2. The isolated microorganism as claimed in claim 1, wherein said microorganism is a mutant strain of *Rhodococcus* sp. ATCC39484.

3. A *Rhodococcus* sp. SD826 (FERM BP-7305) strain.

4. The isolated microorganism according to claim 1, wherein said microorganism has been treated with a mutagen so as to inactivate or reduce the activity of the microorganism to convert a cyano group into an amide group.

5. The isolated microorganism according to claim 4, wherein said mutagen is selected from the group consisting of an alkylating agent, a nucleotide analog, an intercalating agent and ultraviolet radiation.

6. The microorganism of claim 1, wherein said microorganism is obtained by a method comprising the steps of:
(i) providing a microorganism belonging to the genus *Rhodococcus* having an endogenous activity of converting a cyano group of a nitrile compound into a carboxyl group by at least two reaction routes, wherein a first reaction route is a one-stage reaction route catalyzed by a nitrilase, and wherein a second reaction route is a two-stage reaction route catalyzed by a nitrile hydratase and an amidase, wherein said nitrile hydratase produces an amide;
(ii) mutating said microorganism; and
(iii) screening for a mutant microorganism having an endogenous activity of converting a cyano group into a carboxyl group and being defective or reduced in an endogenous activity of converting a cyano group into an amide group.

7. A method for producing the microorganism of claim 1 comprising the steps of:
(i) providing a microorganism belonging to the genus *Rhodococcus* having an endogenous activity of converting a cyano group of a nitrile compound into a carboxyl group by at least two reaction routes, wherein a first reaction route is a one-stage reaction route catalyzed by a nitrilase, and wherein a second reaction route is a two-stage reaction route catalyzed by a nitrile hydratase and an amidase, wherein said nitrile hydratase produces an amide;
(ii) mutating said microorganism; and
(iii) screening for a mutant microorganism having an endogenous activity of converting a cyano group into a carboxyl group and being defective or reduced in an endogenous activity of converting a cyano group into an amide group.

8. The isolated microorganism of claim 6, wherein said nitrile compound is a polynitrile compound having at least two cyano groups or is an aromatic polynitrile compound.

9. The isolated microorganism of claim 6, wherein said amide is selected from the group consisting of o-cyanobenzamide, m-cyanobenzamide, and p-cyanobenzamide.

10. The isolated microorganism of claim 6, wherein said nitrile compound is a polynitrile compound having a plurality of cyano groups and said carboxyl group is a cyano carboxylic acid.

11. The isolated microorganism of claim 10, wherein said polynitrile compound is an aromatic polynitrile compound and said cyano carboxylic acid is an aromatic cyano carboxylic acid.

12. The isolated microorganism of claim 11, wherein said aromatic polynitrile compound is selected from the group consisting of o-phthalonitrile, isophthalonitrile, and terephthalonitrile; and wherein said aromatic cyano carboxylic acid is selected from the group consisting of o-cyanobenzoic acid, m-cyanobenzoic acid, and p-cyanobenzoic acid.

13. The isolated microorganism of claim 6, wherein said mutant microorganism produces a carboxylic acid upon contacting said microorganism with said nitrile compound, wherein an amount of by-products produced by said microorganism from the nitrile compound is 0.5 mol % or less of a total amount of said carboxylic acid.

14. The isolated microorganism of claim 6, wherein said mutating is performed with at least one mutagen selected from the group consisting of an alkylating agent, a nucleotide analog, an intercalating agent, and ultraviolet radiation.

15. The isolated microorganism of claim 6, wherein said mutant microorganism is cultured at less than 40° C.

16. The isolated microorganism of claim 1, wherein said microorganism is cultured at less than 40° C.

17. The isolated microorganism of claim 1 comprising a polynucleotide encoding a nitrilase having the amino acid sequence of SEQ ID NO: 2.

18. A process for producing carboxylic acid, comprising converting at least one cyano group of a nitrile compound into a carboxyl group using the microorganism of claim 1.

19. The process for producing carboxylic acid as claimed in claim 18, wherein said microorganism is a mutant strain of *Rhodococcus* sp. ATCC39484.

20. The process for producing carboxylic acid as claimed in claim 19, wherein said microorganism is *Rhodococcus* sp. SD826 (FERM BP-7305).

21. The process for producing carboxylic acid as claimed in claim 18, wherein the nitrile compound is a polynitrile compound having a plurality of cyano groups in the molecule and the carboxylic acid is a cyano carboxylic acid.

22. The process for producing carboxylic acid as claimed in claim 21, wherein the polynitrile compound is an aromatic polynitrile compound and the cyano carboxylic acid is an aromatic cyano carboxylic acid.

23. The process for producing carboxylic acid as claimed in claim 22, wherein the aromatic polynitrile compound is selected from the group consisting of o-phthalonitrile, isophthalonitrile, and terephthalonitrile, and the aromatic cyano carboxylic acid is corresponding o-cyanobenzoic acid, m-cyanobenzoic acid, or p-cyanobenzoic acid.

\* \* \* \* \*